United States Patent
Schweinsberg et al.

(10) Patent No.: US 8,740,995 B1
(45) Date of Patent: Jun. 3, 2014

(54) OXIDATIVE HAIR TREATMENT WITH SILICONE AND BLEACH

(71) Applicant: Henkel AG & Co. KGaA, Duesseldorf (DE)

(72) Inventors: Mathias Schweinsberg, Hamburg (DE); Jisook Baek, Hamburg (DE); Astrid Kleen, Hamburg (DE); Erik Schulze zur Wiesche, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/132,077

(22) Filed: Dec. 18, 2013

(30) Foreign Application Priority Data

Dec. 19, 2012 (DE) .................. 10 2012 223 804

(51) Int. Cl.
*A61Q 5/10* (2006.01)

(52) U.S. Cl.
USPC ............ 8/405; 8/406; 8/407; 8/581; 132/202; 132/208

(58) Field of Classification Search
USPC .............. 8/405, 406, 407, 581; 132/202, 208
See application file for complete search history.

(56) References Cited

U.S. PATENT DOCUMENTS

| | | | |
|---|---|---|---|
| 6,824,764 B2 * | 11/2004 | Devin-Baudoin et al. ... | 424/70.1 |
| 7,220,408 B2 | 5/2007 | Decoster et al. | |
| 7,223,385 B2 | 5/2007 | Gawtrey et al. | |
| 7,485,289 B2 | 2/2009 | Gawtrey et al. | |
| 7,504,094 B2 | 3/2009 | Decoster et al. | |

FOREIGN PATENT DOCUMENTS

| | | |
|---|---|---|
| AU | 2005256329 B2 | 1/2006 |
| DE | 19756454 C1 | 6/1999 |

* cited by examiner

*Primary Examiner* — Eisa Elhilo
(74) *Attorney, Agent, or Firm* — David K. Benson

(57) ABSTRACT

The subject matter of the present invention is a method for oxidative lightening and/or coloring of keratinic fibers, in particular of hair, wherein a) a pretreatment agent that contains at least one 4-morpholinomethyl-substituted silicone of formulas (V) is applied onto the keratinic fibers, in particular onto the hair, b) subsequently, within a time span from one second to 24 hours after step a), a coloring and/or lightening agent is applied onto the keratinic fibers, which agent is obtained by mixing a composition (A) that contains at least one alkalizing agent with a composition (B) that contains, in a cosmetic carrier, at least one oxidizing agent, where the composition (B) contains at least one acylpyridinium derivative of formula (Acylpyr-I),

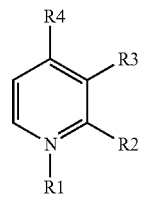

(Acylpyr-I).

20 Claims, No Drawings

OXIDATIVE HAIR TREATMENT WITH SILICONE AND BLEACH

CROSS REFERENCE TO RELATED APPLICATION

This application claims priority to German Patent Application No. 10 2012 223 804.2 filed Dec. 19, 2012, its contents hereby incorporated in its entirety.

TECHNICAL FIELD

The present invention relates to a low-impact method for oxidative lightening and/or coloring of keratinic fibers, in particular of hair, in which the keratinic fibers are protected from oxidizing influences.

BACKGROUND

In the context of oxidative coloring and also oxidative lightening of hair, the problem arises that irritation of the scalp and damage to the keratinic fibers can occur as a result of the aggressive agents. In particular, the natural hydrophobicity of the keratinic fibers is reduced because the coloring agents resp. lightening agents must first make the hair capable of penetration in order to exert their effect. The water-repellent effect on the one hand, however, provides natural protection for the hair; on the other hand, parameters desired by the consumer, such as shine, softness, suppleness, and the "drape" of the hair, are closely linked to it.

In order to overcome the aforesaid disadvantages, so-called pretreatment agents that are intended to protect the hair from aggressive influences are on the market. These often make the hair heavy, however, or negatively affect the outcome of the lightening resp. coloring of the hair that takes place subsequently; in particular, the washing fastness of the color can be degraded by the pretreatment agent.

The object of the present invention is to make available a method for oxidative hair treatment, with a hair-protecting pretreatment, that overcomes the aforesaid disadvantages without counteracting the success of a subsequent oxidative hair treatment. The intention is in particular to make available a method in which the hair is not made heavier, and in which the desired effect can also be achieved in the context of a pretreatment not occurring immediately before the oxidative hair treatment, with the result that the time span between pretreatment and oxidative hair treatment can be extended.

The use of aminated silicones in hair care is established art. They are widely used in shampoos and in particular in conditioners in order to exert care-providing effects therein. EP 1771144 B1, for example, discloses hair-conditioning agents having aminofunctional silicones. The agents described therein are post-treatment agents.

European patents EP 1312334 B1 (aminosilicone and thickener) and EP 1312335 B1 (aminosilicone and conditioner) also disclose hair post-treatment agents.

It has now been found that a pretreatment of the keratinic fibers with special 4-morpholinomethyl-substituted silicones within a specific time period prior to an oxidative hair treatment results in appreciably improved hair protection with no negative effect on the outcome of the oxidative hair treatment. "Hair protection" is to be understood for purposes herein in particular to mean that the structure of the keratinic fibers, in particular of the hair, is less intensely attacked by the oxidizing agent, so that the surface of the fibers resp. of the hair becomes less roughened, the hair ends experience less splitting, and/or less hair breakage occurs. In addition, particularly good color results are also achieved, in particular colors having a high level of washing fastness.

The subject matter of the present invention is, in a first embodiment, a method for oxidative lightening and/or coloring of keratinic fibers, in particular of hair, in which a) a pretreatment agent that contains at least one 4-morpholinomethyl-substituted silicone of formula (V)

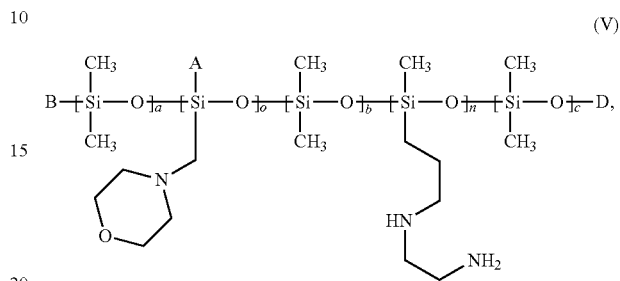

in which

A denotes a structural unit (I), (II), or (III) bound via —O—

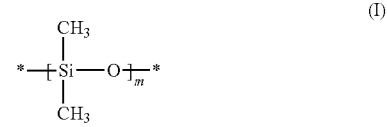

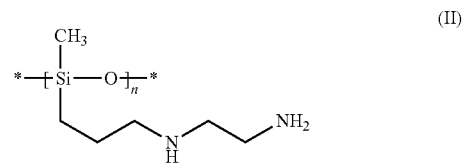

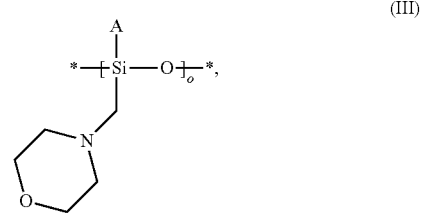

or an oligomeric or polymeric residue bound via —O— containing structural units of formulas (I), (II), or (III), or half of an oxygen atom connecting to a structural unit (III), or denotes —OH,

* denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers from 0 to 990, with the provision that a+b+c>0, and m, n, and o denote integers from 2 to 990 is applied onto the keratinic fibers, in particular the hair, b) subsequently, within a time span from one second to 24 hours after step a), a coloring and/or lightening agent is applied onto the keratinic fibers, which agent is obtained by mixing a composition (A) that contains at least one alkalizing agent with a composition (B) that contains, in a cosmetic carrier, at least one oxidizing agent, where composition (B) contains at least one acylpyridinium derivative of formula (Acylpyr-I)

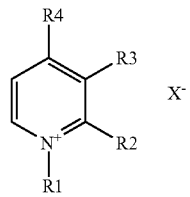

(Acylpyr-I), in which
- R1 denotes a $C_1$ to $C_6$ alkyl group, a $C_2$ to $C_6$ alkenyl group, a $C_2$ to $C_6$ hydroxyalkyl group, a $C_1$ to $C_6$ alkoxy-$C_2$ to $C_6$ alkyl group, a carboxy $C_2$ to $C_6$ alkyl group, an aryl $C_1$ to $C_6$ alkyl group, a heteroaryl $C_1$ to $C_6$ alkyl group, an aryl group, or a heteroaryl group,
- R2, R3, and R4 mutually independently in each case denote hydrogen, a $C_1$ to $C_6$ alkyl group, a halogen atom, or a $C_1$ to $C_6$ acyl group, with the provision that at least one of the residues R2, R3, and R4 denotes a $C_1$ to $C_6$ acyl group, and
- $X^-$ denotes a physiologically acceptable anion.

Pretreatment agents preferably used according to the present invention are characterized in that they contain the at least one 4-morpholinomethyl-substituted silicone of formula (V), which comprises respectively at least one of the structural units of formulas (I), (II), and (III), in a total quantity from about 0.001 to about 5 wt %, preferably about 0.005 to about 2 wt %, particularly preferably about 0.01 to about 1 wt %, extraordinarily preferably about 0.02 to about 0.1 wt %, based in each case on the total weight of the pretreatment agent.

Pretreatment agents preferably used according to the present invention are characterized in that they contain the at least one 4-morpholinomethyl-substituted silicone of formula (V) in a form emulsified in water. Pretreatment agents used particularly preferably contain about 30 to about 98 wt %, preferably about 40 to about 90 wt %, particularly preferably about 50 to about 85 wt %, extraordinarily preferably about 60 to about 80 wt % water, based in each case on the total weight of the pretreatment agent.

Pretreatment agents used particularly preferably are present in the form of an oil-in-water emulsion in which the number-average size of the silicone particles in the emulsion is in the range from about 3 to about 500 nm, preferably in the range from about 5 to about 60 nm.

Structural units of formulas (I), (II), and (III) can be present statistically distributed in the molecule, but the silicones used according to the present invention can also be block copolymers made up of blocks of the individual structural units, in which context the blocks can in turn be present in statistically distributed fashion.

The * on the free valences of structural units (I), (II), or (III) denotes a bond to one of the structural units (I), (II), or (III) or a terminal group B (Si-bound) or D (O-bound).

The silicones used according to the present invention can be trimethylsilyl-terminated at both ends (D=—Si(CH$_3$)$_3$, B=—O—Si(CH$_3$)$_3$), but they can also be dimethylsilylhydroxy- or dimethylsilylmethoxy-terminated at one or two ends. Silicones used particularly preferably in the context of the present invention have at least one terminal dimethylsilylhydroxy group, i.e. are selected from silicones in which
- B=—O—Si(CH$_3$)$_2$OH and D=—Si(CH$_3$)$_3$
- B=—O—Si(CH$_3$)$_2$OH and D=—Si(CH$_3$)$_2$OH
- B=—O—Si(CH$_3$)$_2$OH and D=—Si(CH$_3$)$_2$OCH$_3$
- B=—O—Si(CH$_3$)$_3$ and D=—Si(CH$_3$)$_2$OH
- B=—O—Si(CH$_3$)$_2$OCH$_3$ and D=—Si(CH$_3$)$_2$OH.

These silicones result in exorbitant improvements in the hair properties of the hair treated in accordance with the method according to the present invention, in particular in a tremendous decrease in contact angle.

In structural unit (III), residue A can denote
- a structural unit (I), (II), or (III) bound via —O—, or
- an oligomeric or polymeric residue bound via —O— containing structural units of formulas (I), (II), and (III), or
- half of an oxygen atom connecting to a structural unit (III), or can denote —OH.

In the first case, structural unit (III) becomes one of the structural units (IIIa), (IIIb), or (IIIc):

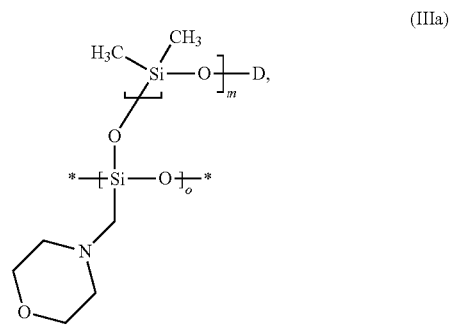
(IIIa)

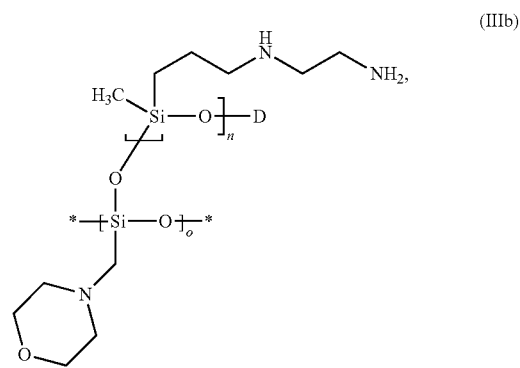
(IIIb)

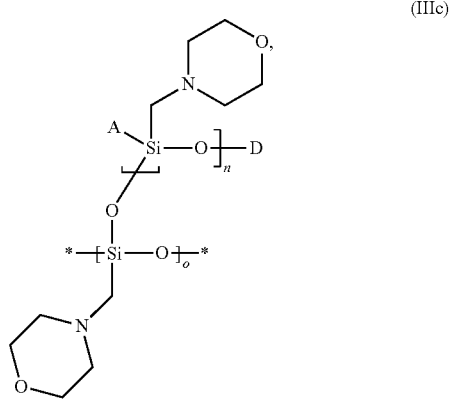
(IIIc)

where m=n=o=1, and A resp. D are as defined above.

In the second case, in the formulas (IIIa), (IIIb), and (IIIc) recited above the indices m, n, and o can denote integers from 2 to 990. The second case also, however, covers oligomeric or polymeric residues that contain at least two different structural units of formulas (I), (II), or (III), as depicted in formula (IIId):

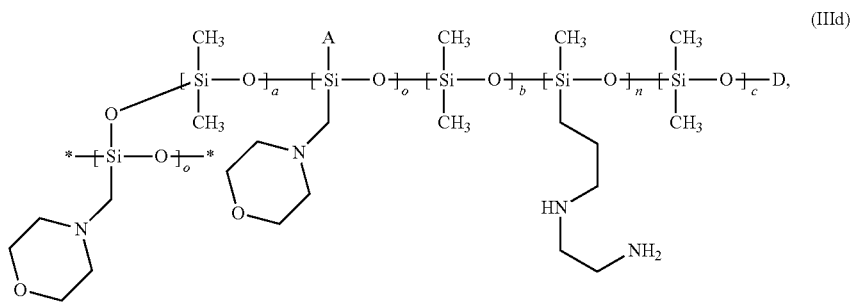
(IIId)

in which a, b, and c denote integers from 0 to 990, with the provision that a+b+c>0, and n and o denote integers from 1 to 990.

In the third case, A denotes half of an oxygen atom connecting to a structural unit (III) (depicted in structural unit (IIIe)) or denotes —OH (depicted in structural unit (IIIf))

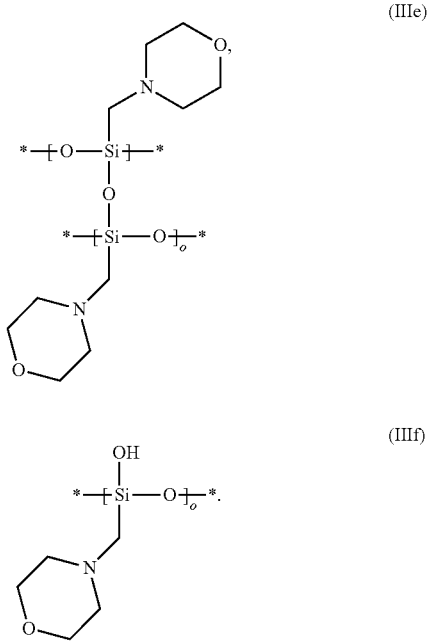

As already mentioned, the structural units of formulas (I), (II), and (III) can preferably be present in statistically distributed fashion. Pretreatment agents preferably used according to the present invention contain at least one 4-morpholinomethyl-substituted silicone of formula (V)

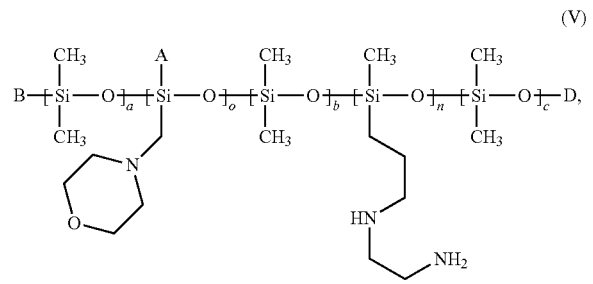

in which
A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers from 0 to 990, with the provision that a+b+c>0, n, and o denote integers from 1 to 990.

Structural formula (V) is intended to illustrate the fact that the siloxane groups n and o do not obligatorily need to be bound directly to an end grouping B resp. D. Instead, in preferred formulas (V) a>0 or b>0, and in particularly preferred formulas (V) a>0 and b>0, i.e. the terminal grouping B resp. D is preferably bound to a dimethylsiloxy grouping. In formula (V) as well, the siloxane units a, b, c, n, and o are preferably statistically distributed.

The silicones represented by formula (V) and used according to the present invention can also be trimethylsilyl-terminated at both ends (D=—Si(CH$_3$)$_3$, B=—O—Si(CH$_3$)$_3$), but they can also be dimethylsilylhydroxy- or dimethylsilylmethoxy-terminated at one or two ends. Silicones used particularly preferably in the context of the present invention have at least one terminal dimethylsilylhydroxy group, i.e. are selected from silicones in which B=—O—Si(CH$_3$)$_2$OH and D=—Si(CH$_3$)$_3$
B=—O—Si(CH$_3$)$_2$OH and D=—Si(CH$_3$)$_2$OH
B=—O—Si(CH$_3$)$_2$OH and D=—Si(CH$_3$)$_2$OCH$_3$
B=—O—Si(CH$_3$)$_3$ and D=—Si(CH$_3$)$_2$OH
B=—O—Si(CH$_3$)$_2$OCH$_3$ and D=—Si(CH$_3$)$_2$OH.

These 4-morpholinomethyl-substituted silicones of formula (V), which respectively comprise at least one of the structural units of formulas (I), (II), and (III), result in surprisingly large improvements in the hair properties of the hair treated in accordance with the method according to the present invention, in particular in tremendously improved hair protection and color protection in the context of oxidative hair coloring.

In formula (V) as well, residue A can denote
a structural unit (I), (II), or (III) bound via —O—, or
an oligomeric or polymeric residue bound via —O— containing structural units of formulas (I), (II), and (III), or
half of an oxygen atom connecting to a structural unit (III), or can denote —OH.

By analogy with the statements regarding structural unit (III), formula (V) is thus refined to one of formulas (Va), (Vb), (Vc), (Vd,), (Ve), or (Vf):

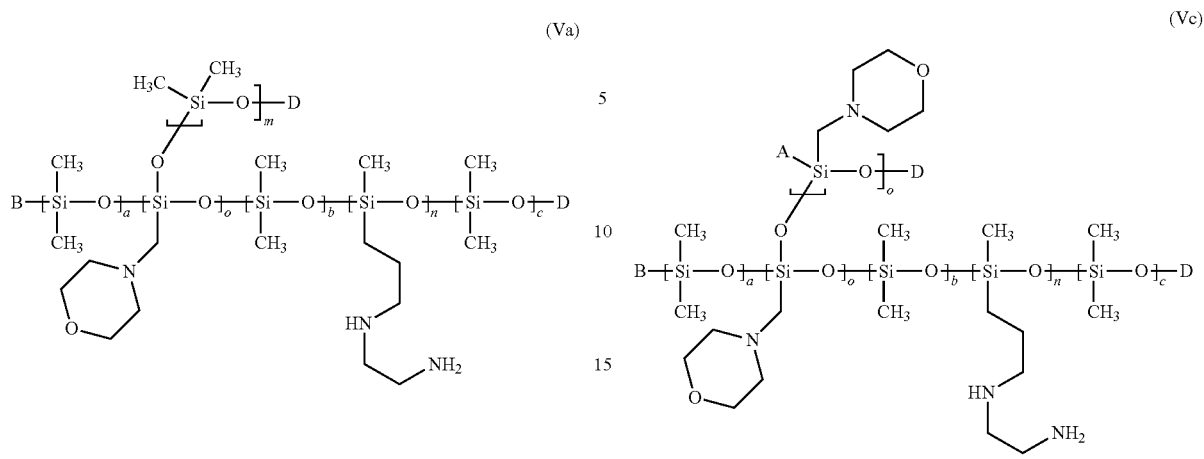
(Va)
(Vc)
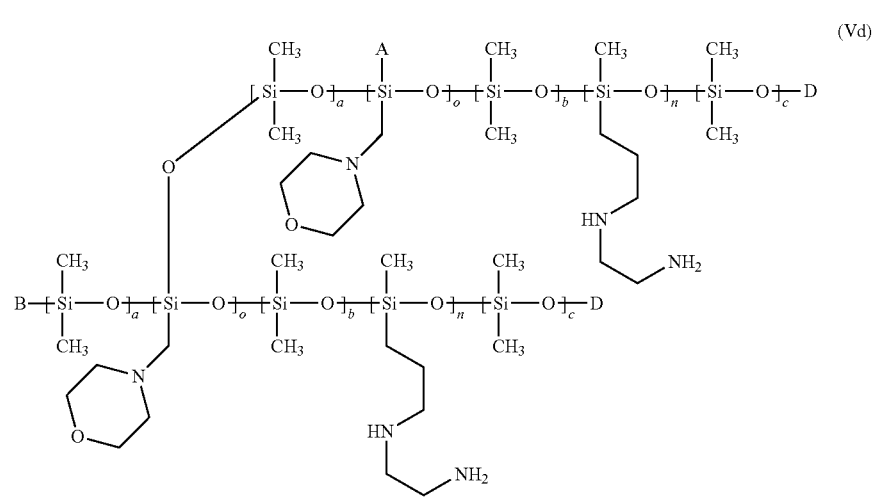
(Vd)
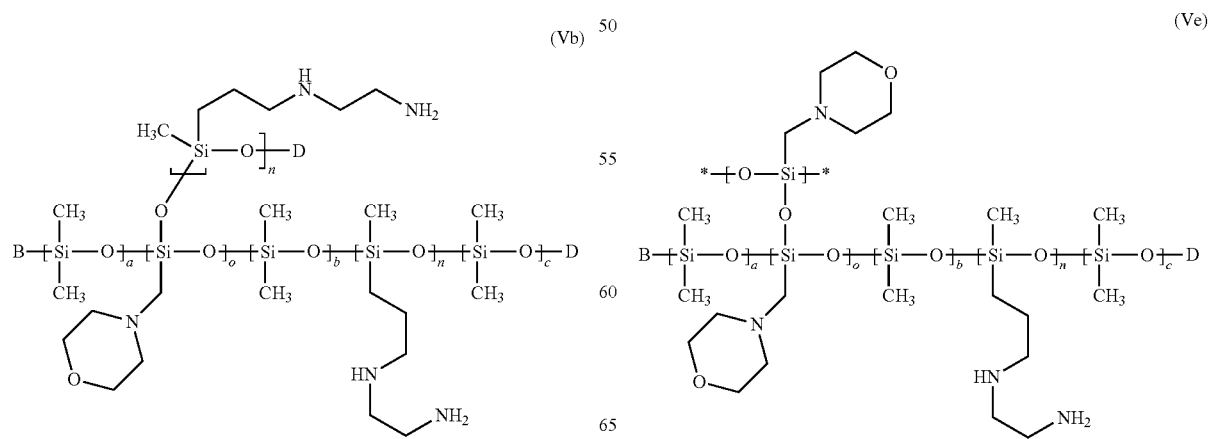
(Vb)
(Ve)

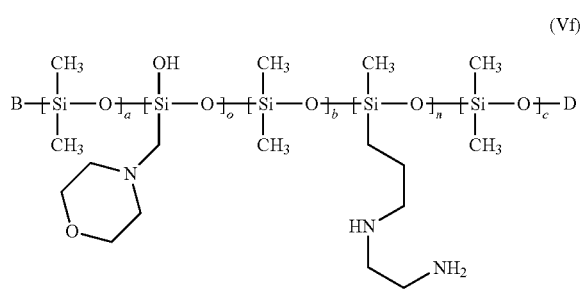

(Vf)

Structural unit (III) resp. the siloxane units o in formulas (V) can, via group A, constitute nest structures resp. partial cage structures when A denotes half of an oxygen atom connecting to a structural unit (III). Pretreatment agents according to the present invention that contain silicones having corresponding 4-morpholinomethyl-substituted silsesquioxane substructures are preferred according to the present invention, since these silicones result in enormously improved hair protection in the context of oxidative hair treatment.

Pretreatment agents preferably used according to the present invention are characterized in that they contain at least one 4-morpholinomethyl-substituted silicone that comprises structural units of formula (VI)

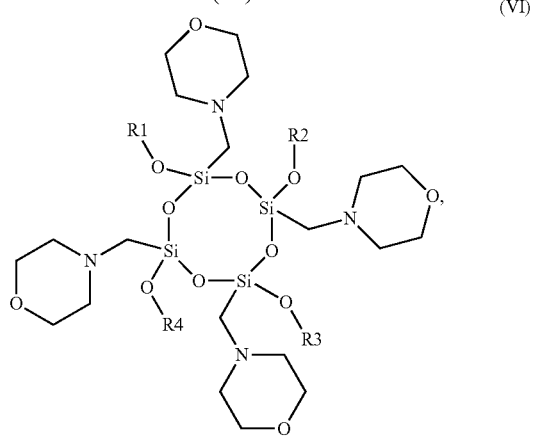

(VI)

in which

R1, R2, R3, and R4 mutually independently denote —H, —CH$_3$, a group D, a structural unit (I), (II), or (III), or an oligomeric or polymeric residue containing structural units of formulas (I), (II), or (III), or two of the residues R1, R2, R3, and R4 denote a structural unit —Si(R6)(R5)-, where R5=—CH$_3$ or a structural unit of formula (I) or (II) or (III) or an oligomeric or polymeric residue containing structural units of formulas (I), (II), or (III), R6=—OH, —CH$_3$, or a structural unit of formula (I) or (II) or (III) or an oligomeric or polymeric residue containing structural units of formulas (I), (II), or (III).

In preferred silicones of formula (VI), at least one of the residues R1, R2, R3, or R4 denotes an oligomeric or polymeric residue containing structural units of formulas (I), (II), or (III).

In further preferred silicones of formula (VI), at least one of the residues R1, R2, R3, or R4 denotes an oligomeric or polymeric residue containing structural units of formulas (I) and (II).

In even further preferred silicones of formula (VI), at least one of the residues R1, R2, R3, or R4 denotes an oligomeric or polymeric residue containing structural units of formulas (I) and (II) and (III).

At least one of the residues R1, R2, R3, or R4 preferably denotes an —[—Si(CH$_3$)$_2$—O]$_m$ grouping, i.e. an oligomer resp. polymer of structural unit (I). In addition, preferably structural unit (II) resp. an oligomer or polymer thereof is never bound in the molecule alone, but instead always in a statistical distribution with further structural units of formula (I) as one of the residues R1, R2, R3, or R4.

Preferred silicones of formula (VI) can be described by formula (VI a)

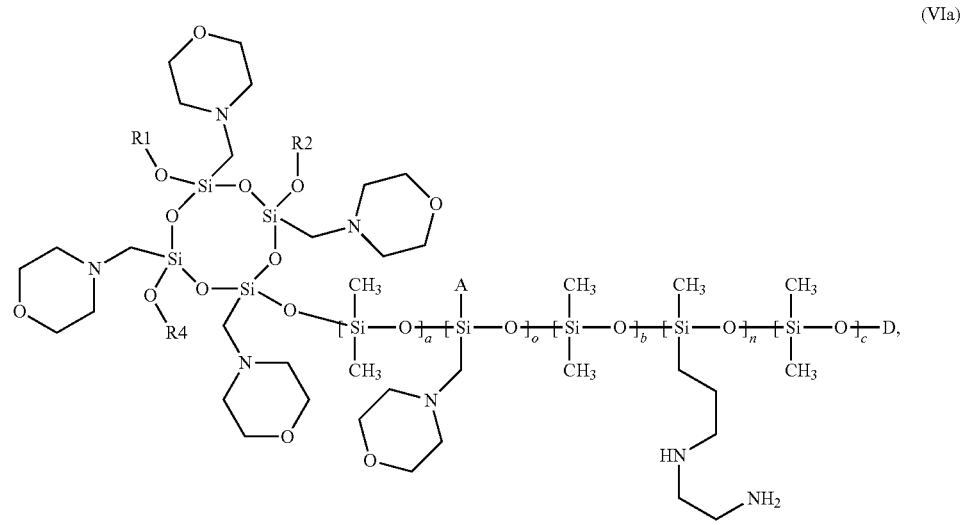

(VIa)

in which

R1, R2, and R4 mutually independently denote —H, —CH$_3$, a group D, a structural unit (I), (II), or (III), or an oligomeric or polymeric residue containing structural units of formulas (I), (II), or (III), or two of the residues R1, R2, and R4 denote a structural unit —Si(R6)(R5)-, where R5=—CH$_3$ or a structural unit of formula (I) or (II) or (III) or an oligomeric or polymeric residue containing structural units of formulas (I), (II), or (III), R6=—OH, —CH$_3$, or a structural unit of formula (I) or (II) or (III) or an oligomeric or polymeric residue containing structural units of formulas (I), (II), or (III), A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, D denotes an —H, —Si(CH$_3$)$_3$, —Si(CH$_3$)$_2$OH, —Si(CH$_3$)$_2$OCH$_3$ group, a, b, and c denote integers from 0 to 990, with the provision that a+b+c>0, n, and o denote integers from 1 to 990.

Further preferred silicones of formula (VI) can be described by formula (VI b)

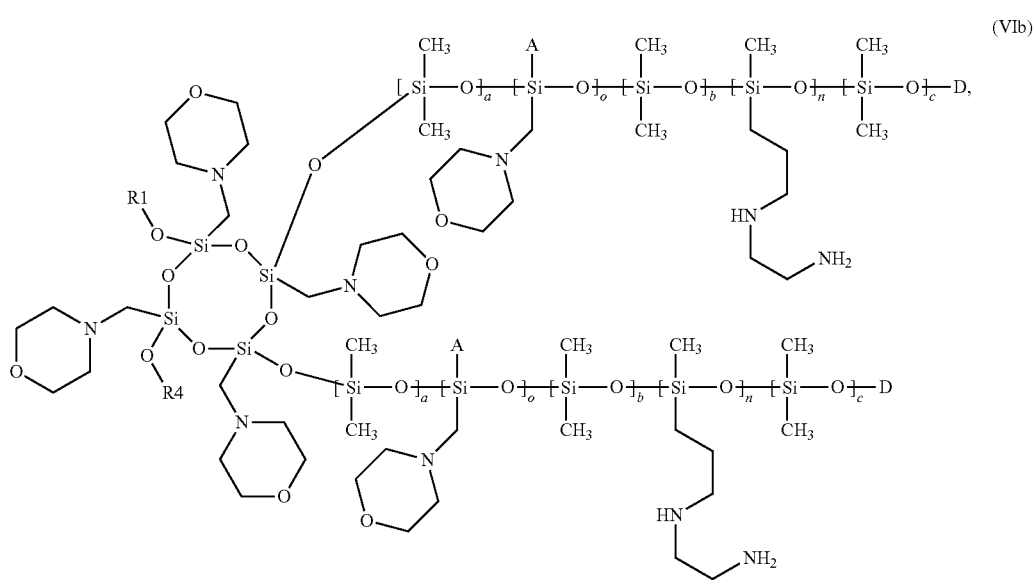

in which the residues and indices are as defined above.

Particularly preferred silicones of formula (VI) can be described by formula (VI c)

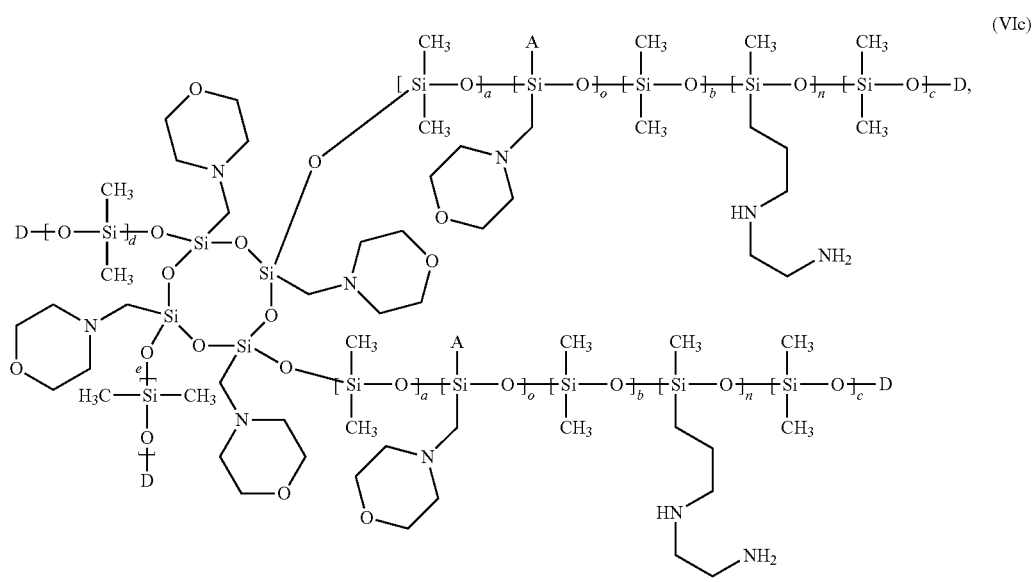

in which the residues and indices are as defined above, and the indices d and e denote integers from 0 to 990.

In formulas (VI a), (VI b), and (VI c), at least one of the groupings D preferably denotes —Si(CH$_3$)$_2$OH.

The silsesquioxane structures can be even more pronounced in the 4-morpholinomethyl-substituted silicones used according to the present invention, which intensifies the advantageous effects.

Particularly preferred pretreatment agents used according to the present invention are characterized in that they contain at least one 4-morpholinomethyl-substituted silicone that comprises structural units of formula (VII)

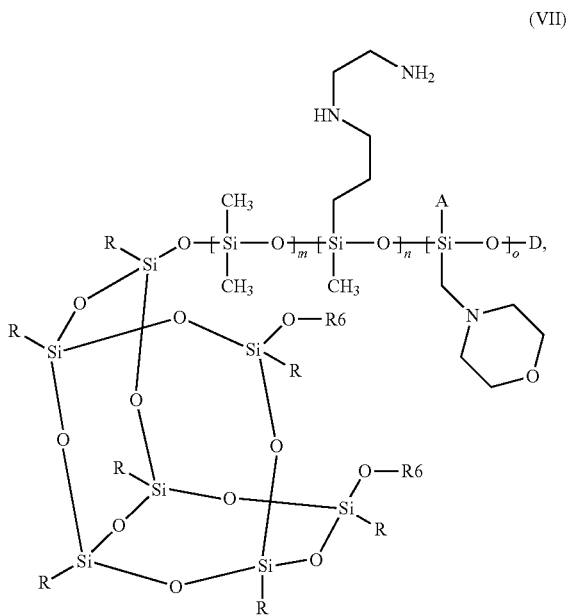

(VII)

in which

A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, D denotes an —H, —Si(CH$_3$)$_3$, —Si(CH$_3$)$_2$OH, —Si(CH$_3$)$_2$OCH$_3$ group, R denotes a 4-morpholinomethyl residue, R6 denotes —H or the grouping

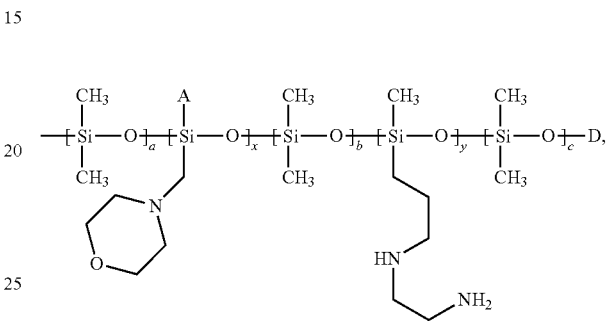

where the siloxane units m, n, and o resp. a, b, c, x, and y are present in statistically distributed fashion.

Pretreatment agents used particularly preferably according to the present invention contain at least one silicone of the following formula (VII a)

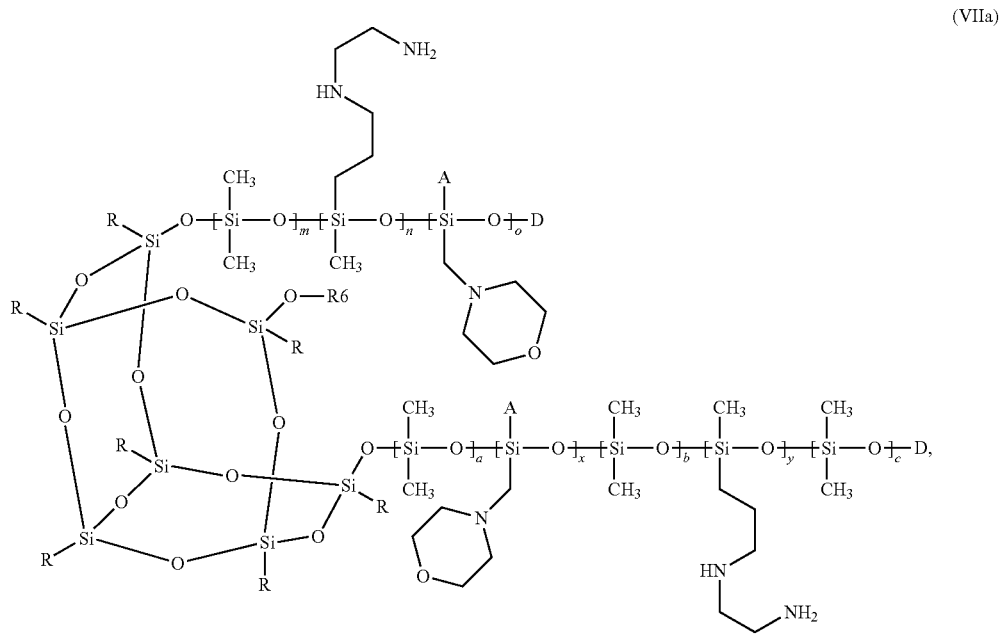

(VIIa)

with the definitions as for formula (VII).

Very particularly preferred pretreatment agents used according to the present invention contain at least one silicone of the following formula (VII b)

(VIIb)

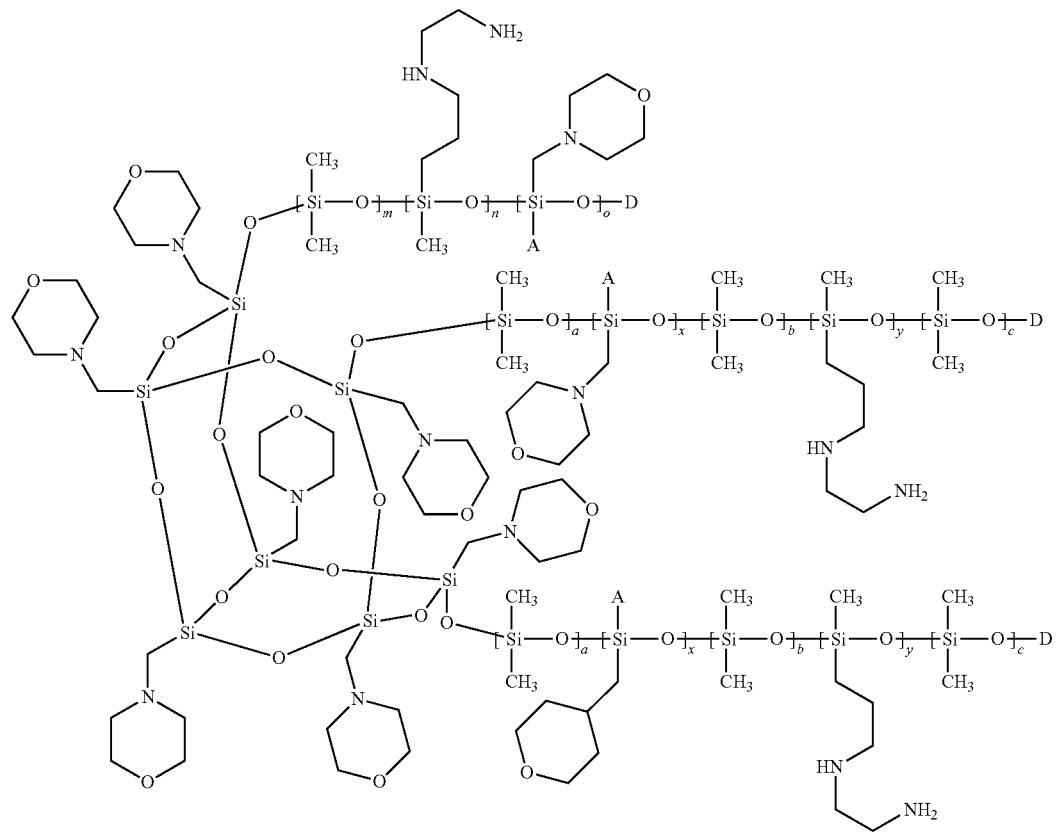

with the definitions as for formula (VII).

In formulas (VII), (VII a), and (VII b), the bridging oxygen atoms between the morpholinomethyl-substituted silicon atoms can also be supplemented by an —[—Si(CH$_3$)$_2$—O]$_m$ grouping, i.e. an oligomer or polymer of structural unit (I). Corresponding pretreatment agents used according to the present invention are those which contain at least one 4-morpholinomethyl-substituted silicone that comprises structural units of formula (VIII)

(VIII)

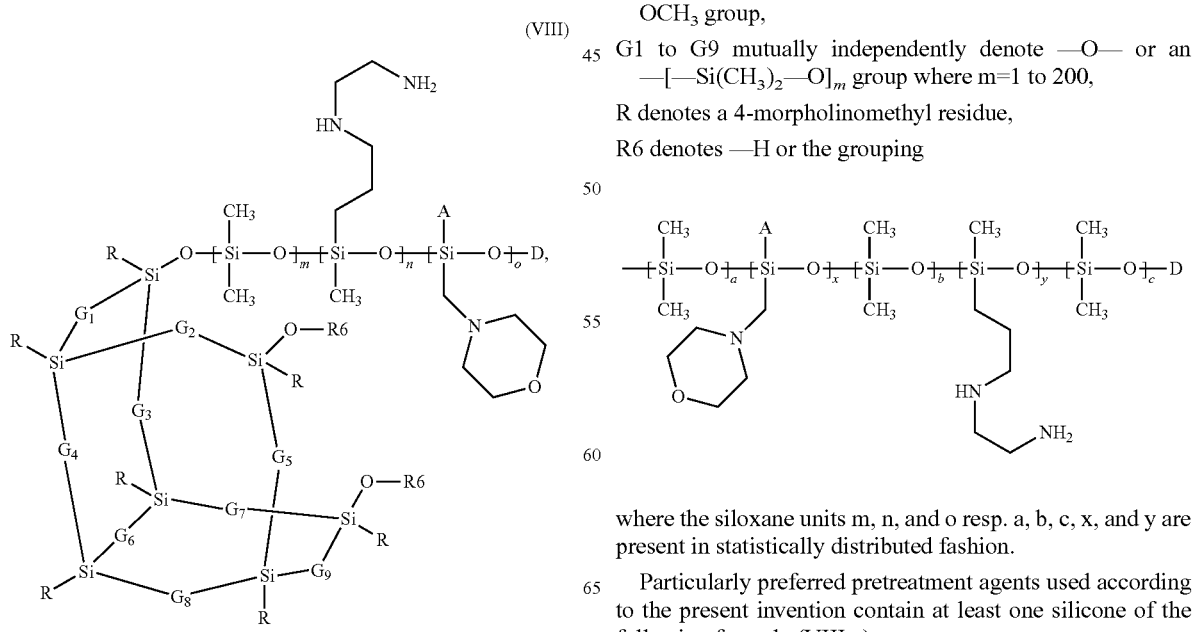

in which

A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, D denotes an —H, —Si(CH$_3$)$_3$, —Si(CH$_3$)$_2$OH, —Si(CH$_3$)$_2$OCH$_3$ group, G1 to G9 mutually independently denote —O— or an —[—Si(CH$_3$)$_2$—O]$_m$ group where m=1 to 200, R denotes a 4-morpholinomethyl residue, R6 denotes —H or the grouping where the siloxane units m, n, and o resp. a, b, c, x, and y are present in statistically distributed fashion.

Particularly preferred pretreatment agents used according to the present invention contain at least one silicone of the following formula (VIII a)

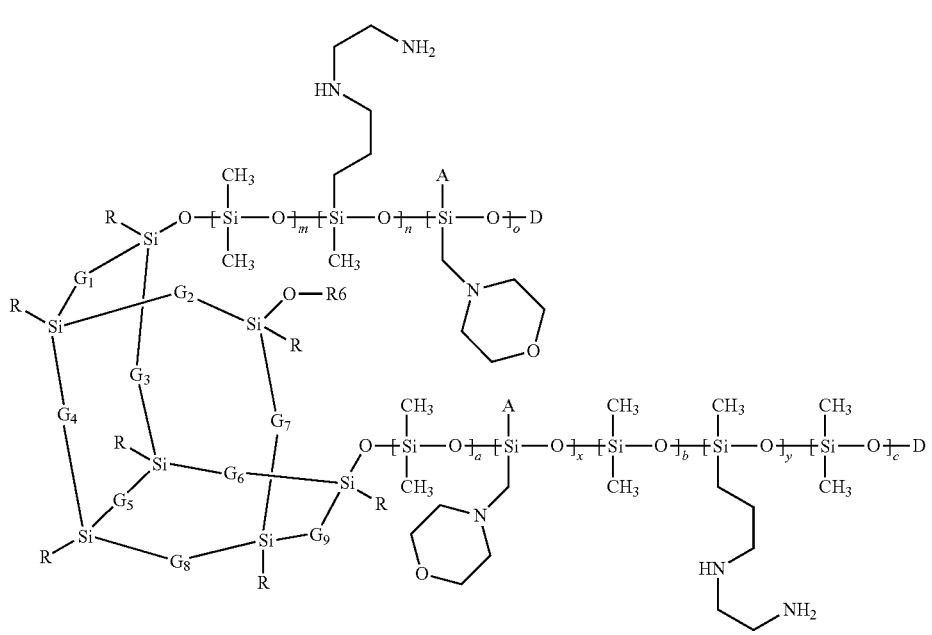

(VIIIa)

with the definitions as for formula (VIII).

Very particularly preferred pretreatment agents used according to the present invention contain at least one silicone of the following formula (VIII b)

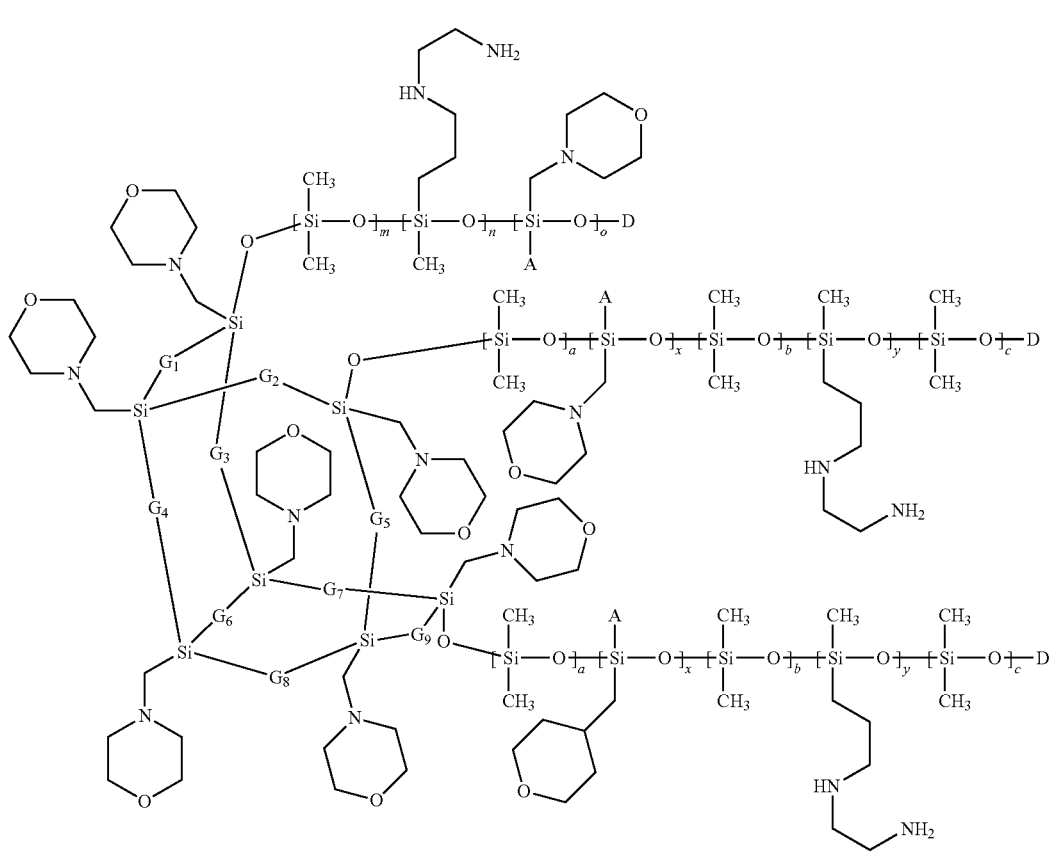

(VIIIb)

with the definitions as for formula (VIII).

Regardless of which special 4-morpholinomethyl-substituted silicone is contained in the pretreatment agents used according to the present invention, pretreatment agents that contain a 4-morpholinomethyl-substituted silicone in which more than 50 mol % of the structural units are dimethylsiloxy units, i.e. in which structural unit (I) makes up at least half of all structural units of the silicone used, are preferred for the method according to the present invention.

In other words, silicones in which m>(n+o) resp. (a+b+c)>(n+o), are preferred.

Even further preferred pretreatment agents used according to the present invention contain a 4-morpholinomethyl-substituted silicone in which more than about 87.5 mol % of the structural units are dimethylsiloxy units, i.e. in which structural unit (I) makes up more than about 875 thousandths of all structural units of the silicone used.

In other words, silicones in which m>8(n+o) resp. (a+b+c)>8(n+o), are preferred.

Even further preferred pretreatment agents used according to the present invention contain a 4-morpholinomethyl-substituted silicone in which more than about 96 mol % of the structural units are dimethylsiloxy units, i.e. in which structural unit (I) makes up at least ninety-six hundredths of all structural units of the silicone used.

In other words, silicones in which m>25(n+o) resp. (a+b+c)>25(n+o), are preferred.

Even further preferred pretreatment agents used according to the present invention contain a 4-morpholinomethyl-substituted silicone in which more than about 98.7 mol % of the structural units are dimethylsiloxy units, i.e. in which structural unit (I) makes up at least nine hundred eighty-seven thousandths of all structural units of the silicone used.

In other words, silicones in which m>77(n+o) resp. (a+b+c)>77(n+o), are preferred.

Even further preferred pretreatment agents used according to the present invention contain a 4-morpholinomethyl-substituted silicone in which more than about 99.5 mol % of the structural units are dimethylsiloxy units, i.e. in which structural unit (I) makes up at least nine hundred ninety-five thousandths of all structural units of the silicone used.

In other words, silicones in which m>200(n+o) resp. (a+b+c)>200(n+o), are preferred.

In summary, preferred pretreatment agents used according to the present invention are characterized in that they contain at least one 4-morpholinomethyl-substituted silicone in which
m>(n+o) resp. (a+b+c)>(n+o), preferably
m>8(n+o) resp. (a+b+c)>8(n+o), particularly preferably
m>25(n+o) resp. (a+b+c)>25(n+o), more preferably
m>77(n+o) resp. (a+b+c)>77(n+o), and in particular
m>200(n+o) resp. (a+b+c)>200(n+o).

A further method preferred according to the present invention is characterized in that the pretreatment agent used in step a) contains hydroxy-terminated 4-morpholinomethyl-substituted silicone(s) in which the molar ratio of hydroxy to alkoxy is in the range from about 0.2:1 to about 0.4:1, preferably in the range from about 1:0.8 to about 1:1.1.

A further method preferred according to the present invention is characterized in that the weight-average molar mass of the 4-morpholinomethyl-substituted silicone of formula (V) used in step a) is in the range from about 2000 to about 1,000,000 gmol$^{-1}$, preferably in the range from about 5000 to about 200,000 gmol$^{-1}$.

The average molar masses of amino-substituted silicones are measurable, for example, by gel permeation chromatography (GPC) at room temperature in polystyrene. Styragel µ columns can be selected as columns, THF as an eluent, and 1 ml/min as a flow rate. Detection is accomplished preferably by refractometry using a UV meter.

4-Morpholinomethyl-substituted silicones of formula (V) that are particularly preferred according to the present invention are contained in the raw material Belsil ADM 8301 E (ex Wacker Silicones) under the name Amodimethicone/Morpholinomethyl Silsesquioxane. Belsil ADM 8301 E represents a microemulsion and is made up of the following constituents: Amodimethicone/Morpholinomethyl Silsesquioxane (about 10 wt %); Trideceth-5 (about 5 wt %); glycerol (about 2.5 wt %); phenoxyethanol (about 0.45 wt %); and water (about 82.05 wt %).

It has become apparent that the method according to the present invention can be further improved if specific nonionic components are likewise contained in the pretreatment agents used according to the present invention. These nonionic components moreover have positive effects on the shelf stability of the pretreatment agents used according to the present invention. Nonionic components that are particularly suitable here are ethoxylates of decanol, undecanol, dodecanol, tridecanol, myristyl alcohol, cetyl alcohol, and/or stearyl alcohol. Ethoxylated tridecanols have proven to be particularly suitable, and are incorporated with particular preference into the pretreatment agents used according to the present invention. Branched ethoxylated tridecanols are particularly preferred, in particular branched tridecanols having 3 to 5 ethylene oxide units in the molecule. Pretreatment agents used particularly preferably according to the present invention contain, based in each case on their weight, about 0.001 to about 5 wt %, preferably about 0.005 to about 3.5 wt %, particularly preferably about 0.01 to about 2 wt %, more preferably about 0.05 to about 1 wt %, and in particular about 0.1 to about 0.5 wt % branched ethoxylated tridecanol, particularly preferably about 0.001 to about 5 wt %, preferably about 0.005 to about 3.5 wt %, particularly preferably about 0.01 to about 2 wt %, more preferably about 0.05 to about 1 wt %, and in particular about 0.1 to about 0.5 wt % branched ethoxylated tridecanol having 3 to 5 ethylene oxide units in the molecule.

Further surfactants and emulsifier agents are preferably not contained, or are contained only in small quantities, in the pretreatment agents used according to the present invention. Pretreatment agents used preferably according to the present invention contain, based on the total weight of the agent, about 0.001 to a maximum of about 6 wt % surfactant(s), the aforementioned ethoxylates of decanol, undecanol, dodecanol, tridecanol, myristyl alcohol, cetyl alcohol, and/or stearyl alcohol being included.

The pretreatment agents used according to the present invention are preferably of low viscosity, i.e. are formulated with a viscosity (measured at about 20° C.) in the range from about 10 to about 2000 mPas, preferably about 20 to about 1000 mPas, particularly preferably about 50 to about 800 mPas. It has moreover been found that thickening polymers can attenuate the effect according to the present invention, so that preferred pretreatment agents used according to the present invention are characterized in that they contain thickening polymers in a total quantity of ≤about 2.5 wt %, preferably ≤about 1 wt %, more preferably ≤about 0.5 wt %, and in particular ≤about 0.01 wt %, based in each case on the weight of the pretreatment agent.

The pretreatment agents used according to the present invention can contain further ingredients. It is preferred in this context to use polyvalent alcohols that have moisture-donating properties. Pretreatment agents used according to the present invention that contain at least one polyvalent alcohol, preferably selected from the group of sorbitol and/or glycerol and/or 1,2-propylene glycol or mixtures thereof, in a total quantity from about 0.05 to about 15 wt %, preferably about 0.1 to about 10 wt %, particularly preferably about 0.15 to about 5 wt %, and in particular about 0.15 to about 1 wt %, based in each case on the weight of the pretreatment agent, are preferred here. For specific utilization sectors it can be advantageous to use only one of the three aforementioned preferred polyvalent alcohols. In most cases, glycerol is preferred. Mixtures of two of the three polyvalent alcohols, or of all three polyvalent alcohols, can nevertheless be preferred in other utilization sectors. A mixture of glycerol, sorbitol, and 1,2-propylene glycol at a weight ratio of about 1:(0.5-1):(0.1-0.5) has proven particularly advantageous here.

Besides sorbitol, glycerol, and 1,2-propylene glycol, further polyvalent alcohols that are suitable are those having at least 2 OH groups, preferably mannitol, xylitol, polyethylene glycol, polypropylene glycol, and mixtures thereof. Among these compounds those having 2 to 12 OH groups, and in particular those having 2, 3, 4, 5, 6, or 10 OH groups, are preferred.

Polyhydroxy compounds having 2 OH groups are, for example, glycol ($CH_2(OH)CH_2OH$) and other 1,2-diols such as $H—(CH_2)_n—CH(OH)CH_2OH$ where n=2, 3, 4, 5, 6, 7, 8, 9, 10, 11, 12, 13, 14, 15, 16, 17, 18, 19, 20. 1,3-Diols such as $H—(CH_2)_n—CH(OH)CH_2CH_2OH$, where n=1, 2, 3, 4, 5, 6, 7, 8, 9, 10, 11, 12, 13, 14, 15, 16, 17, 18, 19, 20, are also usable according to the present invention. The (n,n+1)- resp. (n,n+2)-diols having non-terminal OH groups can likewise be used. Important representatives of polyhydroxy compounds having 2 OH groups are also the polyethylene and polypropylene glycols. Further preferred polyvalent alcohols that can be used are, for example, xylitol, propylene glycols, polyethylene glycols, in particular those having average molecular weights from about 200 to about 800. It is particularly preferred to use glycerol, so that agents that contain no other polyvalent alcohols besides glycerol are particularly preferred.

The use of specific care-providing substances in the pretreatment agents of the method according to the present invention is preferred in terms of pretreatment prior to an oxidative hair treatment.

Pretreatment agents preferably used according to the present invention are characterized in that they additionally contain care-providing substance(s) in a total quantity from about 0.001 to about 10 wt %, preferably about 0.005 to about 7.5 wt %, particularly preferably about 0.01 to about 5 wt %, and in particular about 0.05 to about 2.5 wt %, based in each case on the total weight of the pretreatment agent. Preferred care-providing substance(s) are selected from at least one of the groups recited below:
  i. L-carnitine and/or salts thereof;
  ii. taurine and/or salts thereof;
  iii. niacinamide;
  iv. ubiquinone;
  v. ectoin;
  vi. vitamins;
  vii. flavonoids.

Pretreatment agents used according to the present invention can particularly preferably contain one or more amino acids as a further ingredient. Amino acids usable particularly preferably according to the present invention derive from the group of glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, β-alanine, 4-aminobutyric acid (GABA), betaine, L-cystine (L-Cyss), L-carnitine, L-citrulline, L-theanine, 3',4'-dihydroxy-L-phenylalanine (L-DOPA), 5'-hydroxy-L-tryptophan, L-homocysteine, S-methyl-L-methionine, S-allyl-L-cysteine sulfoxide (L-alliine), L-trans-4-hydroxyproline, L-5-oxoproline (L-pyroglutamic acid), L-phosphoserine, creatine, 3-methyl-L-histidine, L-ornithine; both the individual amino acids and mixtures can be used.

Preferred pretreatment agents used according to the present invention contain one or more amino acids in narrower quantity ranges. Pretreatment agents used according to the present invention are characterized here in that they contain as a care-providing substance about 0.01 to about 5 wt %, preferably about 0.02 to about 2.5 wt %, particularly preferably about 0.05 to about 1.5 wt %, more preferably about 0.075 to about 1 wt %, and in particular about 0.1 to about 0.25 wt % amino acid(s), preferably from the group of glycine and/or alanine and/or valine and/or lysine and/or leucine and/or threonine, based in each case on the total weight of the pretreatment agent.

The pretreatment agent used according to the present invention can be formulated as a low-viscosity water-based emulsion, a spray, a cream, gel, lotion, paste, shampoo, or conditioner.

The method according to the present invention encompasses the application of a pretreatment agent onto keratinic fibers, and an oxidative hair treatment subsequent thereto within a time period from one second to 24 hours.

A great advantage of the pretreatment agents used in step a) is that they are effective not only when utilized immediately prior to oxidative hair treatment, but instead can be utilized up to 24 hours previously with no risk of attenuation of the effect due to external influences. It is thereby possible, for example, to carry out step a) of the method according to the present invention in the morning after shampooing, and to perform the oxidative hair treatment only in the evening.

Methods preferred according to the present invention are characterized in that the time period between method steps a) and b) is from about 2 seconds to about 20 minutes, preferably about 30 seconds to about 10 minutes, particularly preferably about 1 to about 5 minutes.

Further methods preferred according to the present invention are characterized in that the pretreatment agent applied in method step a) is allowed to act on the hair for a time period from about 2 seconds to about 120 minutes, preferably about 5 seconds to about 10 minutes, before method step b) occurs.

Further methods preferred according to the present invention are characterized in that the pretreatment agent applied in method step a) is allowed to act on the hair for a time period from about 2 seconds to about 120 minutes, preferably about 5 seconds to about 10 minutes, before at least one of the following method steps a) i, which occur before method step b), occurs:
  rinsing out the hair;
  drying the hair with a towel;
  allowing the hair to air-dry;
  blow-drying the hair;
  drying the hair with a drying hood;
  combinations thereof.

The drying operation occurs preferably at a temperature from about 20° C. to about 150° C.

Particularly preferably, the drying operation resp. operations are not preceded by rinsing out of the hair. A method preferred according to the present invention is therefore characterized in that no rinsing out of the hair occurs between the application of the pretreatment agent performed in method step a) and the drying operation resp. operations. It can, however, also be preferred according to the present invention first to rinse out the hair after step a) and then to dry it before the treatment step b) occurs.

The method according to the present invention is further characterized in that step b) encompasses the application of a coloring agent and/or lightening agent onto the keratinic fibers, which agent is obtained by mixing a composition (A) that contains at least one alkalizing agent with a composition (B) that contains at least one oxidizing agent in a cosmetic carrier, where composition (B) contains at least one acylpyridinium derivative of formula (Acylpyr-I),

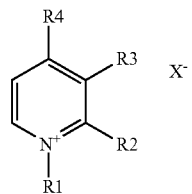

(Acylpyr-I), in which
R1 denotes a $C_1$ to $C_6$ alkyl group, a $C_2$ to $C_6$ alkenyl group, a $C_2$ to $C_6$ hydroxyalkyl group, a $C_1$ to $C_6$ alkoxy-$C_2$ to $C_6$ alkyl group, a carboxy $C_2$ to $C_6$ alkyl group, an aryl $C_1$ to $C_6$ alkyl group, a heteroaryl $C_1$ to $C_6$ alkyl group, an aryl group, or a heteroaryl group,
R2, R3, and R4 mutually independently in each case denote hydrogen, a $C_1$ to $C_6$ alkyl group, a halogen atom, or a $C_1$ to $C_6$ acyl group, with the provision that at least one of the residues R2, R3, and R4 denotes a $C_1$ to $C_6$ acyl group, and
$X^-$ denotes a physiologically acceptable anion.

The composition (B) used in the methods and kits of parts according to the present invention and preferred according to the present invention contains as a first obligatory ingredient at least one acylpyridinium derivative of formula (Acylpyr-I) as explained above. It has been found, surprisingly, that an acylpyridinium derivative of this kind interacts synergistically with the pretreatment used according to the present invention, and resulted in an unexpected reduction in hair damage.

Examples of the aforesaid substituents of the compounds of formula (Acylpyr-I) are recited below, but not in limiting fashion: Examples of $C_1$ to $C_6$ alkyl residues are the groups —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$. Examples of a $C_2$ to $C_6$ alkenyl group are a prop-2-enyl group (allyl group), a 2-methyl-prop-2-enyl group, a but-3-enyl group, a but-2-enyl group, a pent-4-enyl group, or a pent-3-enyl group, the prop-2-enyl group being preferred. Examples of a $C_2$ to $C_6$ hydroxyalkyl group are —$CH_2CH_2OH$, —$CH_2CH_2CH_2OH$, —$CH_2CH(OH)CH_3$, and —$CH_2CH_2CH_2CH_2OH$, the —$CH_2CH_2OH$ group being preferred. Examples of $C_1$ to $C_6$ alkoxy-$C_2$ to $C_6$ alkyl groups are the groups —$CH_2CH_2OCH_3$, —$CH_2CH_2CH_2OCH_3$, —$CH_2CH_2OCH_2CH_3$, —$CH_2CH_2CH_2OCH_2CH_3$, —$CH_2CH_2OCH(CH_3)_2$, —$CH_2CH_2CH_2OCH(CH_3)_2$. Examples of a carboxy-$C_1$ to $C_6$ alkyl group are the carboxymethyl group, the 2-carboxyethyl group, or the 3-carboxypropyl group. Examples of aryl-$C_1$ to $C_6$ alkyl groups are the benzyl group and the 2-phenylethyl group. Examples of a heteroaryl-$C_1$ to $C_6$ alkyl group are the pyridin-2-ylmethyl group, the pyridin-3-ylmethyl group, the pyridin-4-ylmethyl group, the pyrimidin-2-ylmethyl group, the pyrrol-1-ylmethyl group, the pyrrol-1-ylethyl group, the pyrazol-1-ylmethyl group, or the pyrazol-1-ylethyl group. Examples of an aryl group are the phenyl group, the 1-naphthyl group, or the 2-naphthyl group. Examples of a heteroaryl group are the pyridin-2-yl group, the pyridin-3-yl group, the pyridin-4-yl group, the pyrimidin-2-yl group, the pyrrol-1-yl group, the pyrrol-2-yl group, the pyrazol-1-yl group, the pyrazol-3-yl group, or the pyrazol-4-yl group. Examples of a $C_1$ to $C_6$ acyl group are acetyl (1-oxoethyl), 1-oxopropyl, 1-oxobutyl, 1-oxopentyl, 1-oxo-2,2-dimethylpropyl, and 1-oxohexyl.

In an embodiment of the present invention, those compounds according to formula (Acylpyr-I) in which the residue R1 of the general structure (Acylpyr-I) denotes a $C_1$ to $C_6$ alkyl group, a $C_2$ to $C_6$ alkenyl group, or a $C_2$ to $C_6$ hydroxyalkyl group, are preferred. It is preferred according to the present invention if the residue R1 denotes a $C_1$ to $C_6$ alkyl group, preferably methyl, ethyl, n-propyl, or isopropyl, and particularly preferably methyl.

It has been found that the acetylpyridinium derivatives according to formula (I) possess particularly advantageous properties according to the present invention if they carry the acyl group in either the 2- or the 4-position on the pyridine ring. Preferred compounds of formula (Acylpyr-I) are furthermore those compounds in which either residue R2 or residue R4 denotes a $C_1$ to $C_6$ acyl group, preferably an acetyl group. It is furthermore preferred if one of the residues R2 or R4 denotes an acetyl group, while the other of these residues, and residue R3, each denote hydrogen. A further embodiment of the present invention is characterized in that the agent contains, as an acetylpyridinium derivative according to formula (I), at least one 2-acetylpyridinium derivative and/or 4-acetylpyridinium derivative.

Suitable acetylpyridinium derivatives are, in this context, the physiologically acceptable salts that contain, as a cation, an acetylpyridinium derivative selected from 4-acetyl-1-methylpyridinium, 4-acetyl-1-allylpyridinium, 4-acetyl-1-(2-hydroxyethyl)pyridinium, 2-acetyl-1-methylpyridinium, 2-acetyl-1-allylpyridinium, and 2-acetyl-1-(2-hydroxyethyl) pyridinium.

It is preferred if the anion $X^-$ according to formula (Acylpyr-I) is selected from halide, in particular chloride, bromide, and iodide, benzenesulfonate, p-toluenesulfonate, $C_1$ to $C_4$ alkylsulfonate, trifluoromethanesulfonate, acetate, trifluoroacetate, perchlorate, hemisulfate, hydrogen sulfate, tetrafluoroborate, hexachlorophosphate, or tetrachlorozincate. It is particularly preferred according to the present invention if the anion $X^-$ denotes hydrogen sulfate, p-toluenesulfonate, benzenesulfonate, or acetate. Extraordinarily preferably, the anion $X^-$ is p-toluenesulfonate.

Methods and kits particularly preferred according to the present invention are those characterized in that the acylpyridinium derivative according to formula (Acylpyr-I) is selected from the group constituted from 4-acetyl-1-methylpyridinium-p-toluenesulfonate, 4-acetyl-1-methylpyridinium benzenesulfonate, 4-acetyl-1-methylpyridinium hydrogen sulfate, 4-acetyl-1-methylpyridinium acetate, 4-acetyl-1-allylpyridinium-p-toluenesulfonate, 4-acetyl-1-allylpyridinium benzenesulfonate, 4-acetyl-1-allylpyridinium hydrogen sulfate, 4-acetyl-1-allylpyridinium acetate, 2-acetyl-1-methylpyridinium-p-toluenesulfonate, 2-acetyl-1-methylpyridinium benzenesulfonate, 2-acetyl-1-methylpyridinium hydrogen sulfate, 2-acetyl-1-methylpyridinium acetate, 2-acetyl-1-allylpyridinium-p-toluenesulfonate, 2-acetyl-1-allylpyridinium benzenesulfonate, 2-acetyl-1-allylpyridinium hydrogen sulfate, and 2-acetyl-1-allylpyridinium acetate.

Methods and kits preferred according to the present invention are characterized in that they contain as an acylpyridinium derivative according to formula (Acylpyr-I) a compound selected from 4-acetyl-1-methylpyridinium-p-toluenesulfonate and/or 2-acetyl-1-methylpyridinium-p-toluenesulfonate, in particular 4-acetyl-1-methylpyridinium-p-toluenesulfonate.

Those methods and kits which are characterized in that they one or more acylpyridinium derivative(s) of formula (Acylpyr-I), in a total quantity from about 0.001 to about 15 wt %, preferably from about 0.01 to about 10 wt %, and particularly preferably from about 0.1 to about 5 wt %, based in each case on the total weight of the coloring and/or lightening agent applied in method step b), have proven to be preferred according to the present invention.

Composition (B) used in the method according to the present invention contains as a second obligatory ingredient at least one oxidizing agent. Preferred oxidizing agents are selected from peroxo compounds, preferably selected from hydrogen peroxide, a solid addition compound of hydrogen peroxide with inorganic or organic compounds, such as sodium perborate, sodium percarbonate, magnesium percarbonate, sodium percarbamide, polyvinylpyrrolidone.n $H_2O_2$ (n is a positive number greater than 0), urea peroxide, and melamine peroxide, furthermore selected from diammonium peroxodisulfate (also referred to as ammonium persulfate), disodium peroxodisulfate (also referred to as sodium persulfate), and dipotassium peroxodisulfate (also referred to as potassium persulfate), and from mixtures of these oxidizing agents. Oxidizing agents used with very particular preference according to the present invention are aqueous hydrogen peroxide solutions. The concentration of a hydrogen peroxide solution is determined on the one hand by regulatory provisions and on the other hand by the desired effect; about 6- to about 12-weight-percent solutions in water are preferably used. Methods preferred according to the present invention are characterized in that the composition (B) that is used contains, based on its weight, about 1 to about 24 wt %, preferably about 4 to about 10 wt %, particularly preferably about 3 to about 6 wt % hydrogen peroxide (calculated as 100% $H_2O_2$).

The cosmetically acceptable carrier of composition (B) is preferably aqueous, alcoholic, or aqueous alcoholic. "Aqueous alcoholic" carriers are to be understood for purposes of the present invention as aqueous compositions containing about 3 to about 70 wt % of a $C_1$ to $C_4$ alcohol based on the total weight of composition (B), in particular ethanol resp. isopropanol. Compositions (B) preferred according to the present invention can additionally contain further organic solvents such as, for example, 4-methoxybutanol, ethyl diglycol, 1,2-propylene glycol, n-propanol, n-butanol, n-butylene glycol, glycerol, diethylene glycol monoethyl ether, and diethylene glycol mono-n-butyl ether. All water-soluble organic solvents are preferred in this context. An "aqueous" carrier contains, for purposes of the invention, water in a total quantity from about 35 to about 97 wt %, particularly preferably about 50 to about 90 wt %, particularly preferably about 60 to about 80 wt %, based in each case on the total weight of composition (B).

By preference according to the present invention, composition (B) has a weakly acid pH, preferably a pH value from about pH 2 to about pH 6, particularly preferably from about pH 2.5 to about pH 4.5, extraordinarily preferably from about pH 3.0 to about pH 4.0. The pH values for purposes of the present invention are pH values that were measured at a temperature of about 22° C. One skilled in the art is familiar, for purposes of adjusting the pH, with common acidifying and alkalizing agents. Acidifying agents preferred according to the present invention are edible acids such as, for example, citric acid, acetic acid, malic acid, or tartaric acid, as well as dilute mineral acids.

The coloring and/or lightening agent applied in method step b) should be notable for very good miscibility of the two compositions (A) and (B). The coloring and/or lightening agent resulting from mixing is intended to have sufficient viscosity that the agent on the one hand can be applied easily, but on the other hand remains at the location of action during utilization and does not flow off the fibers.

To achieve sufficient thickening, the use of polymeric thickeners whose thickening properties change with pH is preferred. This property can be utilized particularly advantageously if the polymeric thickener is contained in the acidic oxidizing agent composition (B), since this agent experiences a large change in pH upon mixing to yield the coloring and/or lightening agent. Composition (B) therefore preferably contains at least one anionic polymeric thickener that results in an appreciable increase in viscosity at an alkaline pH. Preferably crosslinked, but also uncrosslinked, homo- or copolymers of acrylic acid or methacrylic acid are particularly preferred as such anionic polymeric thickening agents.

It has furthermore proven to be advantageous if composition (B) contains at least one stabilizer or complexing agent. Particularly preferred stabilizers are phenacetin, alkali benzoates (sodium benzoate), and salicylic acid.

The use of so-called complexing agents in composition (B) is also preferred according to the present invention. Complexing agents are substances that can complex metal ions. Preferred complexing agents are so-called chelate complexing agents, i.e. substances that form cyclic compounds with metal ions, where an individual ligand occupies more than one coordination site on a central atom, i.e. is at least "double-toothed." Usual chelate complexing agents that are preferred in the context of the present invention are, for example, polyoxycarboxylic acids, polyamines, ethylenediaminetetraacetic acid (EDTA), nitrilotriacetic acid (NTA), and hydroxyethanediphosphonic acids resp. alkali salts thereof. Also usable according to the present invention are complexing polymers, i.e. polymers that carry either in the main chain itself, or laterally thereto, functional groups that can act as ligands and react with suitable metal atoms, usually accompanied by the formation of chelate complexes. The polymer-bound ligands of the resulting metal complexes can derive from only one macromolecule or else can belong to different polymer chains. Complexing agents preferred according to the present invention are nitrogen-containing polycarboxylic acids, in particular EDTA, and phosphonates, by preference hydroxyalkane- resp. aminoalkanephosphonates, and in particular 1-hydroxyethane-1,1-diphosphonate (HEDP) resp. the di- or tetrasodium salt thereof, and/or ethylenediaminetetramethylenephosphonate (EDTMP) resp. the hexasodium salt thereof, and/or diethylenetriaminepentamethylenephosphonate (DTPMP) resp. the hepta- or octasodium salt thereof. Dipicolinic acid is likewise preferred.

Composition (A) used in the method according to the present invention and in the kit of parts contains as an obligatory ingredient at least one alkalizing agent. Oxidative coloring processes on keratin fibers usually proceed in an alkaline environment. In order to minimize stress on the keratin fibers and also on the skin, however, it is not desirable to establish too high a pH. It is therefore preferred if the pH of the coloring agent and/or lightening agent used in step b) is between 7 and 11, in particular in the range from 8 to 10.5. The pH values for purposes of the present invention are pH values that have been measured at a temperature of 22° C.

The alkalizing agents usable according to the present invention in order to establish the preferred pH can be selected from the group of ammonia, basic amino acids, alkali hydroxides, alkanolamines, alkali metal metasilicates, alkali phosphates, and alkali hydrogen phosphates. Lithium, sodium, potassium preferably serve as alkali metal ions, in particular sodium or potassium.

The basic amino acids usable as alkalizing agents are preferably selected from the group of L-arginine, D-arginine, D,L-arginine, L-lysine, D-lysine, D,L-lysine, particularly preferably L-arginine, D-arginine, D,L-arginine used as an alkalizing agent for purposes of the invention.

The alkali hydroxides usable as alkalizing agents are preferably selected from the group of sodium hydroxide and potassium hydroxide.

The alkanolamines usable as alkalizing agents are preferably selected from primary amines having a $C_2$ to $C_6$ alkyl basic structure that carries at least one hydroxyl group. Particularly preferred alkanolamines are selected from the group that is constituted from 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Alkanolamines very particularly preferred according to the present invention are selected from the group of: 2-aminoethan-1-ol, 2-amino-2-methylpropan-1-ol, and 2-amino-2-methylpropane-1,3-diol.

For oxidative coloring methods, it is usual that, shortly before application onto the fibers, in particular the hair, a coloring composition (A), which contains at least one alkalizing agent as well as one or more oxidation dye precursors and optionally one or more substantive dyes, is mixed with an aqueous oxidizing-agent-containing composition (B) to yield a ready-to-use coloring agent and is then applied onto the fibers, in particular the hair.

For oxidative lightening methods, it is usual that, shortly before application onto the fibers, in particular the hair, a lightening composition (A), which contains at least one alkalizing agent as well as optionally one or more substantive dyes, is mixed with an aqueous oxidizing-agent-containing composition (B) to yield a ready-to-use coloring agent and is then applied onto the fibers, in particular the hair.

The coloring and/or lightening composition (A) and the oxidizing-agent-containing composition (B) are usually coordinated with one another in such a way that with a mixing ratio of about 1:1 (based on parts by weight) an initial concentration of hydrogen peroxide from about 0.5 to about 12 wt %, preferably about 2 to about 10 wt %, particularly preferably about 3 to about 6 wt % hydrogen peroxide (calculated as 100% $H_2O_2$) is present in the hair coloring agent, based on the weight of the coloring and/or lightening agent. It is, however, equally possible to coordinate the coloring and/or lightening composition (A) and the oxidizing-agent-containing composition (B) with one another in such a way that the concentrations necessary in the ready-to-use coloring and/or lightening agent are obtained by means of mixing ratios other than about 1:1, for example by a weight-related mixing ratio of about 1:2 or about 1:3 or even about 2:3. Methods preferred according to the present invention are characterized in that the ready-to-use coloring and/or lightening agent used in method step b) contains an initial quantity of hydrogen peroxide from about 0.5 to about 12 wt %, preferably about 2 to about 10 wt %, particularly preferably about 3 to about 6 wt % hydrogen peroxide (calculated as 100% $H_2O_2$), based on the weight of the coloring and/or lightening agent.

Methods and kits of parts preferred according to the present invention are characterized in that the ready-to-use coloring and/or lightening agent used in method step b) contains at least one cosmetic oil in a total quantity from about 5 to about 50 wt %, preferably about 8 to about 40 wt %, particularly preferably about 12 to about 30 wt %, extraordinarily preferably about 15 to about 25 wt %, based in each case on the weight of the coloring and/or lightening agent.

The use of hydrogen peroxide or addition products thereof with organic resp. inorganic compounds is often insufficient for a coloring operation that requires considerable lightening of very dark hair. A combination of hydrogen peroxide and peroxodisulfate salts (persulfate salts) is generally used in such cases. Preferred persulfate salts are ammonium peroxydisulfate, potassium peroxydisulfate, sodium peroxydisulfate, and mixtures thereof.

The at least one persulfate salt is contained preferably in a total quantity from about 0.1 to about 25 wt %, particularly preferably in a total quantity from about 1 to about 15 wt %, based on the weight of the ready-to-use coloring agent.

Further methods and kits of parts preferred according to the present invention are characterized in that the composition (B) contains at least one cosmetic oil in a total quantity from about 10 to about 80 wt %, based on the weight of composition (B). The cosmetic oil is liquid under standard conditions (20° C., 1013.25 mbar); essential oils and perfume oils resp. fragrances are not included among the cosmetic oils. The cosmetic oils that are liquid under standard conditions are not miscible with water. "Essential oils" are understood according to the present invention as mixtures of volatile components that are produced by steam distillation from vegetable raw materials, e.g. citrus oils. When a "cosmetic oil" is discussed in herein, this always refers to a cosmetic oil that is not a fragrance and not an essential oil, is liquid under standard conditions, and is not miscible with water.

The definition of a "fragrance" for purposes herein corresponds to the definition usual in the art, as may be gathered from the RÖMPP Chemie Lexikon [Chemical Lexicon] as of December 2007. According to the latter, a fragrance is a chemical compound having an odor and/or taste that excites the receptors of the hair cells of the olfactory system (adequate stimulus). The physical and chemical properties necessary for this are a low molar mass of at most 300 g/mol, a high vapor pressure, minimal water solubility and high lipid solubility, as well as weak polarity and the presence of at least one osmophoric group in the molecule. In order to distinguish volatile low-molecular-weight substances that are usually (and also for purposes of the present Application) viewed and utilized not as fragrances but instead principally as solvents, for example ethanol, propanol, isopropanol, and acetone, from fragrances according to the present invention, fragrances according to the present invention have a molar mass from about 74 to about 300 g/mol, contain at least one osmophoric group in the molecule, and have an odor and/or taste, i.e. they excite the receptors of the hair cells of the olfactory system.

Cosmetic oils preferred according to the present invention are selected from natural and synthetic hydrocarbons, particularly preferably from paraffin oils, $C_{18}$ to $C_{30}$ isoparaffins, in particular isoeicosane, polyisobutenes, and polydecenes, which are obtainable, for example, under the name Emery® 3004, 3006, 3010 or under the name Ethylflo® from Albemarle or Nexbase® 2004G from Nestle, further selected from $C_8$ to $C_{16}$ isoparaffins, in particular from isodecane, isododecane, isotetradecane, and isohexadecane as well as mixtures thereof, as well as 1,3-di-(2-ethylhexyl)cyclohexane (obtainable e.g. under the trade name Cetiol® S from BASF).

Further cosmetic oils preferred according to the present invention are selected from benzoic acid esters of linear or branched $C_{8-22}$ alkanols. Benzoic acid $C_{12}$ to $C_{15}$ alkyl esters, obtainable e.g. as the commercial product Finsolv® TN, benzoic acid isostearyl esters, obtainable e.g. as the commercial product Finsolv® SB, ethylhexyl benzoate, obtainable e.g. as the commercial product Finsolv® EB, and benzoic acid octyldodecyl esters, obtainable e.g. as the commercial product Finsolv® BOD, are particularly preferred.

Further cosmetic oils preferred according to the present invention are selected from fatty alcohols having 6 to 30 carbon atoms, which are unsaturated or branched and saturated or branched and unsaturated. The branched alcohols are often also referred to as "Guerbet alcohols," since they are obtainable via the Guerbet reaction. Preferred alcohol oils are 2-hexyldecanol (Eutanol® G 16), 2-octyldodecanol (Eutanol® G), 2-ethyhexyl alcohol, and isostearyl alcohol.

Further preferred cosmetic oils are selected from mixtures of Guerbet alcohols and Guerbet alcohol esters, e.g. the commercial product Cetiol® PGL (2-hexyldecanol and 2-hexyldecyl laurate).

Further cosmetic oils preferred according to the present invention are selected from triglycerides triesters of glycerol) of linear or branched, saturated or unsaturated, optionally hydroxylated $C_{8-30}$ fatty acids. The use of natural oils, e.g. amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, blackcurrant seed oil, jojoba oil, linseed oil, macadamia nut oil, corn oil, almond oil, marula oil, evening primrose oil, olive oil, palm oil, palm kernel oil, para nut oil, pecan nut oil, peach kernel oil, rapeseed oil, castor oil, sea buckthorn pulp oil, sea buckthorn seed oil, sesame oil soy oil, sunflower oil, grapeseed oil, walnut oil, wild rose oil, wheat germ oil, and the liquid components of coconut oil and the like, can be particularly preferred. Synthetic triglyceride oils are also preferred, however, in particular Capric/Caprylic Triglycerides, e.g. the commercial products Myritol® 318, Myritol® 331 (BASF), or Miglyol® 812 (Hüls) having unbranched fatty acid esters, as well as glyceryl triisostearine having branched fatty acid esters.

Further cosmetic oils particularly preferred according to the present invention are selected from dicarboxylic acid esters of linear or branched $C_2$ to $C_{10}$ alkanols, in particular diisopropyl adipate, di-n-butyl adipate, di-(2-ethylhexyl) adipate, dioctyl adipate, diethyl-/di-n-butyl/dioctyl sebacate, diisopropyl sebacate, dioctyl malate, dioctyl maleate, dicaprylyl maleate, diisooctyl succinate, di-2-ethylhexyl succinate, and di-(2-hexyldecyl)succinate.

Further cosmetic oils particularly preferred according to the present invention are selected from esters of linear or branched, saturated or unsaturated fatty alcohols having 2 to 30 carbon atoms with linear or branched, saturated or unsaturated fatty acids having 2 to 30 carbon atoms, which can be hydroxylated. These include 2-hexyldecyl stearate (Eutanol® G 16 S), 2-hexyldecyl laurate, isodecyl neopentanoate, isononyl isononanoate, 2-ethylhexyl palmitate (Cegesoft® C 24), and 2-ethylhexyl stearate (Cetiol® 868). Also preferred are isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyl octanoic acid 2-butyl octanoate, diisotridecyl acetate, n-butyl stearate, n-hexyl laurate, n-decyl oleate, oleyl oleate, oleyl erucate, erucyl oleate, erucyl erucate, ethylene glycol dioleate, and ethylene glycol dipalmitate.

Further cosmetic oils preferred according to the present invention are selected from addition products of 1 to 5 propylene oxide units with mono- or polyvalent $C_{8-22}$ alkanols such as octanol, decanol, decanediol, lauryl alcohol, myristyl alcohol, and stearyl alcohol, e.g. PPG-2 Myristyl Ether and PPG-3 Myristyl Ether (Witconol® APM).

Further cosmetic oils preferred according to the present invention are selected from addition products of at least 6 ethylene oxide and/or propylene oxide units with mono- or polyvalent $C_{3-22}$ alkanols such as glycerol, butanol, butanediol, myristyl alcohol, and stearyl alcohol, which can be esterified if desired, e.g. PPG-14 Butyl Ether (Ucon Fluid® AP), PPG-9 Butyl Ether (Breox® B25), PPG-10 Butanediol (Macol® 57), PPG-15 Stearyl Ether (Arlamol® E), and glycereth-7 diisonoanoate.

Further cosmetic oils preferred according to the present invention are selected from $C_8$ to $C_{22}$ fatty alcohol esters of monovalent or polyvalent $C_2$ to $C_7$ hydroxycarboxylic acids, in particular the esters of glycolic acid, lactic acid, malic acid, tartaric acid, citric acid, and salicylic acid. Such esters based on linear $C_{14/15}$ alkanols, e.g. $C_{12}$ to $C_{15}$ alkyl lactate, and on $C_{12/13}$ alkanols branched in the 2-position, can be obtained under the trade name Cosmacol® from Nordmann, Rassmann GmbH & Co., Hamburg, in particular the commercial products Cosmacol® ESI, Cosmacol® EMI, and Cosmacol® ETI.

Further cosmetic oils preferred according to the present invention are selected from symmetrical, asymmetrical, or cyclic esters of carbonic acid with $C_{3-22}$ alkanols, $C_{3-22}$ alkanediols, or $C_{3-22}$ alkanetriols, e.g. dicaprylyl carbonate (Cetiol® CC), or the esters according to the teaching of DE 19756454 A1, in particular glycerol carbonate.

Further cosmetic oils that can be preferred according to the present invention are selected from esters of dimers of unsaturated $C_{12}$ to $C_{22}$ fatty acids (dimer fatty acids) with monovalent linear, branched, or cyclic $C_2$ to $C_{18}$ alkanols or with polyvalent linear or branched $C_2$ to $C_6$ alkanols.

Further cosmetic oils that are suitable according to the present invention are selected from among the silicone oils that include, for example, dialkyl- and alkylarylsiloxanes such as e.g. cyclopentasiloxane, cyclohexasiloxane, dimethylpolysiloxane, and methyphenylpolysiloxane, but also hexamethyldisiloxane, octamethyltrisiloxane, and decamethyltetrasiloxane. Volatile silicone oils, which can be cyclic, can be preferred, for example octamethylcyclotetrasiloxane, decamethylcyclopentasiloxane, and dodecamethylcyclohexasiloxane, as well as mixtures thereof such as those contained, for example, in the commercial products DC 244, 245, 344, and 345 of Dow Corning. Also suitable are volatile linear silicone oils, in particular hexamethyldisiloxane ($L_2$), octamethyltrisiloxane ($L_3$), decamethyltetrasiloxane ($L_4$), as well as any mixtures of two or three of $L_2$, $L_3$, and/or $L_4$, preferably mixtures such as those contained e.g. in the commercial products DC 2-1184, Dow Corning® 200 (0.65 cSt), and Dow Corning® 200 (1.5 cSt) of Dow Corning. Preferred nonvolatile silicone oils are selected from higher-molecular-weight linear dimethylpolysiloxanes, obtainable commercially e.g. under the name Dow Corning® 190, Dow Corning® 200 Fluid, having kinematic viscosities (25° C.) in the range from 5 to 100 cSt, preferably 5 to 50 cSt, or even 5 to 10 cSt, and dimethylpolysiloxane having a kinematic viscosity (25° C.) of approximately 350 cSt.

It can be extraordinarily preferred according to the present invention to use mixtures of the aforementioned cosmetic oils.

Preferred compositions (B) used according to the present invention are characterized in that the cosmetic oil is selected from natural and synthetic hydrocarbons, particularly preferably from paraffin oils, $C_{18}$ to $C_{30}$ isoparaffins, in particular isoeicosane, polyisobutenes, and polydecenes, $C_8$ to $C_{16}$ isoparaffins, and 1,3-di-(2-ethylhexyl)cyclohexane; benzoic acid esters of linear or branched C$_{8-22}$ alkanols; fatty alcohols having 6 to 30 carbon atoms, which are unsaturated or branched and saturated or branched and unsaturated; triglycerides of linear or branched, saturated or unsaturated, optionally hydroxylated C$_{8-30}$ fatty acids, in particular natural oils; dicarboxylic acid esters of linear or branched C$_2$ to C$_{10}$ alkanols; esters of linear or branched, saturated or unsaturated fatty alcohols having 2 to 30 carbon atoms with linear or branched, saturated or unsaturated fatty acids having 2 to 30 carbon atoms, which can be hydroxylated; addition products of 1 to 5 propylene oxide units with mono- or polyvalent C$_{8-22}$ alkanols; addition products of at least 6 ethylene oxide and/or propylene oxide units with mono- or polyvalent C$_{3-22}$ alkanols; C$_8$ to C$_{22}$ fatty alcohol esters of monovalent or polyvalent C$_2$ to C$_7$ hydroxycarboxylic acids; symmetrical, asymmetrical, or cyclic esters of carbonic acid with C$_{3-22}$ alkanols, C$_{3-22}$ alkanediols, or C$_{3-22}$ alkanetriols; esters of dimers of unsaturated C$_{12}$ to C$_{22}$ fatty acids (dimer fatty acids) with monovalent linear, branched, or cyclic C$_2$ to C$_{18}$ alkanols or with polyvalent linear or branched C$_2$ to C$_6$ alkanols; silicone oils; and mixtures of the aforementioned substances.

Preferred methods and kits of parts according to the present invention are characterized in that the composition (B) used according to the present invention contains at least one cosmetic oil in a total quantity from about 12 to about 70 wt %, preferably about 14 to about 60 wt %, particularly preferably about 15 to about 52 wt %, and extraordinarily preferably about 17 to about 35 wt %, based in each case on the weight of composition (B).

Further preferred methods and kits of parts according to the present invention are characterized in that the composition (B) used according to the present invention contains at least one surfactant.

When selecting surfactants suitable according to the present invention, it is particularly preferred to use a mixture of surfactants in order to allow optimum adjustment of the stability of the oxidizing agent compositions (B) used according to the present invention.

Preferred methods and kits of parts according to the present invention are characterized in that the surfactant contained in composition (B) is selected from nonionic surfactants and anionic surfactants and from mixtures thereof. Nonionic surfactants used with particular preference are selected from castor oil ethoxylated with 20 to 100 mol ethylene oxide per mol, ethoxylated C$_8$ to C$_{24}$ alkanols having 10 to 100 mol ethylene oxide per mol, ethoxylated C$_8$ to C$_{24}$ carboxylic acids having 10 to 100 mol ethylene oxide per mol, sorbitan monoesters, ethoxylated with 20 to 100 mol ethylene oxide per mol, of linear saturated and unsaturated C$_{12}$ to C$_{30}$ carboxylic acids, which can be hydroxylated, in particular those of myristic acid, palmitic acid, stearic acid, or mixtures of these fatty acids, alkylmono- and -oligoglycosides having 8 to 22 carbon atoms in the alkyl residue and ethoxylated analogs thereof, and mixtures of the aforesaid substances.

Castor oil ethoxylated with 40 to 80 mol ethylene oxide per mol is preferably contained in the compositions (B) preferably used according to the present invention.

The ethoxylated C$_8$ to C$_{24}$ alkanols have the formula R$^1$O(CH$_2$CH$_2$O)$_n$H, where R$^1$ denotes a linear or branched alkyl residue and/or alkenyl residue having 8 to 24 carbon atoms, and n (the average number of ethylene oxide units per molecule) denotes numbers from 10 to 100, preferably 10 to 30, particularly preferably 15 to 25 mol ethylene oxide per 1 mol caprylyl alcohol, 2-ethylhexyl alcohol, capryl alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, and brassidyl alcohol, as well as industrial mixtures thereof. Adducts of 10 to 100 mol ethylene oxide with industrial fatty alcohols having 12 to 18 carbon atoms, for example coconut, palm, palm kernel, or tallow fatty alcohol, are also suitable. Laureth-10, Laureth-12, Laureth-15, Laureth-20, Laureth-30, Myreth-10, Myreth-12, Myreth-15, Myreth-20, Myreth-30, Ceteth-10, Ceteth-12, Ceteth-15, Ceteth-20, Ceteth-30, Steareth-10, Steareth-12, Steareth-15, Steareth-20, Steareth-30, Oleth-10, Oleth-12, Oleth-15, Oleth-20, Oleth-30, Ceteareth-10, Ceteareth-15, Ceteareth-12, Ceteareth-15, Ceteareth-20, Ceteareth-30, as well as Coceth-10, Coceth-12, Coceth-15, Coceth-20, and Coceth-30, are particularly preferred.

The ethoxylated C$_8$ to C$_{24}$ carboxylic acids have the formula R$^1$O(CH$_2$CH$_2$)$_n$H, where R$^1$O denotes a linear or branched, saturated or unsaturated acyl residue having 8 to 24 carbon atoms and n (the average number of ethylene oxide units per molecule) denotes numbers from 10 to 100, preferably 10 to 30 mol ethylene oxide per 1 mol caprylic acid, 2-ethylhexanoic acid, capric acid, lauric acid, isotridecanoic acid, myristic acid, cetylic acid, palmitoleic acid, stearic acid, isostearic acid, oleic acid, elaidic acid, petroselic acid, arachidic acid, gadoleic acid, behenic acid, erucic acid, and brassidic acid, as well as industrial mixtures thereof. Adducts of 10 to 100 mol ethylene oxide with industrial fatty acids having 12 to 18 carbon atoms, for example coconut, palm, palm kernel, or tallow fatty acid, are also suitable. PEG-50 monostearate, PEG-100 monostearate, PEG-50 monooleate, PEG-100 monooleate, PEG-50 monolaurate, and PEG-100 monolaurate are particularly preferred.

Preferred sorbitan monoesters, ethoxylated with 20 to 100 mol ethylene oxide per mol, of linear saturated and unsaturated C$_{12}$ to C$_{30}$ carboxylic acids, which can be hydroxylated, are selected from Polysorbate-20, Polysorbate-40, Polysorbate-60, and Polysorbate-80.

C$_8$ to C$_{22}$ alkylmono- and -oligoglycosides are also preferably used. C$_8$ to C$_{22}$ alkylmono- and -oligoglycosides represent known, commercially usual surfactants and emulsifier agents. They are manufactured in particular by reacting glucose or oligosaccharides with primary alcohols having 8 to 22 carbon atoms. With regard to the glycoside residue, both monoglycosides in which a cyclic sugar residue is bound glycosidically to the fatty alcohol, and oligomeric glycosides having a degree of oligomerization up to approximately 8, preferably 1 to 2, are suitable. The degree of oligomerization is a statistical average that is based on a homolog distribution that is usual for industrial products of this kind. Products that are obtainable under the name Plantacare® contain a glucosidically bound C$_8$ to C$_{16}$ alkyl group on an oligoglucoside residue whose average degree of oligomerization is 1 to 2, in particular 1.2 to 1.4. Particularly preferred C$_8$ to C$_{22}$ alkyl mono- and -oligoglycosides are selected from octyl glucoside, decyl glucoside, lauryl glucoside, palmityl glucoside, isostearyl glucoside, stearyl glucoside, arachidyl glucoside, and behenyl glucoside, as well as mixtures thereof. The acyl glucamides derived from glucamine are also suitable as nonionic oil-in-water emulsifier agents.

Anionic surfactants suitable in the compositions (B) used according to the present invention are all anionic surface-active substances suitable for use on the human body, which comprise an anionic group imparting water solubility, for example a carboxylate, sulfate, sulfonate, or phosphate group, and a lipophilic alkyl group having approximately 8 to 30 carbon atoms, preferably 8 to 24 carbon atoms, in the molecule. Glycol ether or polyglycol ether groups, ester, ether, and amide groups, and hydroxyl groups can additionally be contained in the molecule. Examples of suitable anionic surfactants are, in each case in the form of the sodium, potassium, and ammonium salts and the mono-, di, and trialkanolammonium salts having 2 to 4 carbon atoms in the alkanol group: linear and branched fatty acids having 8 to 30 carbon atoms (soaps), polyethoxylated ethercarboxylic acids, acyl sarcosides, acyl taurides, acyl isethionates, sulfosuccinic acid mono- and dialkyl esters and sulfosuccinic acid monoalkylpolyoxyethyl esters having 1 to 6 ethylene oxide groups, linear alkanesulfonates, linear alpha-olefinsulfonates, sulfonates of unsaturated fatty acids having up to 6 double bonds, alpha-sulfo fatty acid methyl esters of fatty acids, $C_8$ to $C_{20}$ alkyl sulfates and $C_8$ to $C_{20}$ alkyl ether sulfates having up to 15 oxyethyl groups, mixtures of surface-active hydroxysulfonates, sulfated hydroxyalkyl polyethylene glycol ethers and/or hydroxyalkylene propylene glycol ethers, esters of tartaric acid or citric acid with ethoxylated or propoxylated fatty alcohols, optionally polyethoxylated alkyl and/or alkenyl ether phosphates, sulfated fatty acid alkylene glycol esters, as well as monoglyceride sulfates and monoglyceride ether sulfates.

Preferred anionic surfactants are soaps, $C_8$ to $C_{20}$ alkyl sulfates, $C_8$ to $C_{20}$ alkyl ether sulfates, and $C_8$ to $C_{20}$ ether carboxylic acids having 8 to 20 carbon atoms in the alkyl group and up to 12 ethylene oxide groups in the molecule. Sodium cetearyl sulfate is particularly preferred.

Preferably the total quantity of at least one surfactant in the oxidizing agent composition (B) is about 0.1 to about 5 wt %, preferably about 0.5 to about 3 wt %, and particularly preferably about 1 to about 2 wt %, based in each case on the total weight of the oxidizing agent composition (B).

Particularly preferably, the oxidizing agent composition (B) used according to the present invention contains a total of about 0.1 to about 5 wt %, preferably about 0.5 to about 3 wt %, and particularly preferably about 1 to about 2 wt %, of a mixture of nonionic and anionic surfactants, based in each case on the total weight of the oxidizing agent composition (B).

Further preferred methods according to the present invention are characterized in that the composition (B) used according to the present invention contains at least one linear saturated alkanol having 12 to 30 carbon atoms.

Preferred linear saturated alkanols having 12 to 30 carbon atoms, in particular having 16 to 22 carbon atoms, are selected from cetyl alcohol, stearyl alcohol, arachidyl alcohol, behenyl alcohol, and lanolin alcohol, as well as mixtures of these alkanols. Alkanol mixtures particularly preferred according to the present invention are those obtainable upon industrial hydrogenation of vegetable and animal fatty acids. The total quantity in the oxidizing agent composition (B) of at least one linear saturated alkanol having 12 to 30 carbon atoms is about 0.1 to about 10 wt %, preferably about 0.5 to about 7 wt %, and particularly preferably about 3 to about 5 wt %, based in each case on the total weight of the oxidizing agent composition (B).

Further preferred methods and kits of parts according to the present invention are characterized in that the composition (B) used according to the present invention contains:
about 1 to about 24 wt %, preferably about 4 to about 10 wt %, particularly preferably about 3 to about 6 wt % hydrogen peroxide (calculated as 100% $H_2O_2$), furthermore
at least one cosmetic oil in a total quantity from about 12 to about 70 wt %, preferably about 14 to about 60 wt %, particularly preferably about 15 to about 52 wt %, and extraordinarily preferably about 17 to about 35 wt %,
furthermore at least one surfactant in a total quantity from about 0.1 to about 5 wt %, preferably about 0.5 to about 3 wt %, and particularly preferably about 1 to about 2 wt %, as well as
at least one linear saturated alkanol having 12 to 30 carbon atoms, in a total quantity from about 0.1 to about 10 wt %, preferably about 0.5 to about 7 wt %, and particularly preferably about 3 to about 5 wt %, where all "wt %" indications refer to the weight of composition (B).

The composition (A) used in the method according to the present invention contains, as ingredients that are obligatory for coloring methods and optional for lightening methods, at least one oxidation dye precursor of the developer type and at least one oxidation dye precursor of the coupler type.

Oxidation dye precursors can be divided in terms of their reaction behavior into two categories: the so-called developer components and coupler components.

Coupler components alone do not produce any significant color in the context of oxidative coloring, but instead always require the presence of developer components. Developer components can form, with themselves, the actual dye.

The developer and coupler components are usually used in free form. In the case of substances having amino groups, however, it can be preferred to use them in salt form, in particular in the form of the hydrochlorides or hydrobromides or the sulfates.

It has been found, surprisingly, that hair coloring results with particularly good washing fastness could be achieved with the method according to the present invention using at least one oxidation dye precursor of the developer type and at least one oxidation dye precursor of the coupler type.

Particularly preferred developer components are selected from at least one compound of the group that is constituted from p-phenylenediamine, p-toluoylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, the physiologically acceptable salts of these compounds, and mixtures of these developer components and developer component salts.

Very particularly preferred developer components are selected from 4,5-diamino-1-(2-hydroxyethyl)pyrazole, p-toluoylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine,
and mixtures of these compounds as well as physiologically acceptable salts thereof. 4,5-Diamino-1-(2-hydroxyethyl)pyrazole and physiologically acceptable salts thereof are extraordinarily preferred.

The developer components are used preferably in a total quantity from about 0.01 to about 20 wt %, particularly preferably about 0.2 to about 10 wt %, and extraordinarily preferably about 0.6 to about 5 wt %, based in each case on the weight of composition (A).

The developer components are used preferably in a total quantity from about 0.005 to about 10 wt %, particularly preferably about 0.1 to about 5 wt %, and extraordinarily preferably about 0.3 to about 2.5 wt %, based in each case on the weight of the ready-to-use coloring agent.

The term "ready-to-use coloring and/or lightening agent" is understood for purposes herein as the mixture of composition (A) and composition (B). A suitable cosmetic carrier for composition (A) is, in particular, a cream base.

Coupler components for purposes of the invention allow at least one chemical residue of the coupler to be substituted with the oxidized form of the developer component, in which context a covalent bond forms between the coupler component and developer component. Couplers are preferably cyclic compounds that carry on the cycle at least two groups selected from (i) optionally substituted amino groups, and/or (ii) hydroxyl groups. If the cyclic compound is a six-membered ring (preferably aromatic), the aforesaid groups are then located preferably in the ortho or meta position with respect to one another.

Preferred methods according to the present invention are characterized in that the at least one oxidation dye precursor of the coupler type is selected from one of the following classes:
- 3-aminophenol (m-aminophenol) and/or derivatives thereof,
- 3-aminoaniline (m-diaminobenzene) and/or derivatives thereof,
- 2-aminoaniline (1,2-diaminobenzene; o-diaminobenzene) and/or derivatives thereof,
- 2-aminophenol (o-aminophenol) and/or derivatives thereof,
- naphthalene derivatives having at least one hydroxy group,
- di-resp. trihydroxybenzene and/or derivatives thereof,
- pyridine derivatives,
- pyrimidine derivatives,
- monohydroxyindole derivatives and/or monoaminoindole derivatives,
- monohydroxyindoline derivatives and/or monoaminoindoline derivatives pyrazolone derivatives such as e.g. 1-phenyl-3-methylpyrazol-5-one,
- morpholine derivatives such as e.g. 6-hydroxybenzomorpholine or 6-aminobenzomorpholine,
- quinoxaline derivatives such as e.g. 6-methyl-1,2,3,4-tetrahydroquinoxaline.

Mixtures of two or more compounds from one or more of these classes are likewise preferred according to the present invention in the context of this embodiment.

Additional coupler components particularly preferred according to the present invention are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl) amino-2-methylphenol, 2,4-dichloro-3-aminophenol, 2-aminophenol, 3-phenylenediamine, 2-(2,4-diaminophenoxy) ethanol, 1,3-bis-(2,4-diaminophenoxy)propane, 1-methoxy-2-amino-4-(2'-hydroxyethylamino)benzene (=2-amino-4-hydroxyethylaminoanisole), 1,3-bis-(2,4-diaminophenyl) propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl) amino]-2-methoxy-5-methylphenyl}amino)ethanol, 2-({3-[(2-hydroxyethyl)amino]-4,5-dimethylphenyl}amino) ethanol 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynapthalene, 4-hydroxyindole, 6-hydroxyindole, 7-hydroxyindole, 4-hydroxyindoline, 6-hydroxyindoline, 7-hydroxyindoline, or mixtures of these compounds, or the physiologically acceptable salts of the aforesaid compounds.

Very particularly preferred in this context are 3-aminophenol, resorcinol, 2-methylresorcinol, 5-amino-2-methylphenol, 2-(2,4-diaminophenoxy)ethanol, 1,3-bis-(2,4-diaminophenoxy)propane, 1-methoxy-2-amino-4-(2'-hydroxyethylamino)benzene, 2-amino-3-hydroxypyridine, and 1-naphthol, as well as physiologically acceptable salts thereof and mixtures of the components recited.

The at least one coupler component is used preferably in a total quantity from about 0.01 to about 20 wt %, particularly preferably about 0.2 to about 10 wt %, and extraordinarily preferably about 0.6 to about 5 wt %, based in each case on the weight of composition (A).

The at least one coupler component is used preferably in a total quantity from about 0.005 to about 10 wt %, preferably about 0.1 to about 5 wt %, and extraordinarily preferably about 0.3 to about 2.5 wt %, based in each case on the weight of the ready-to-use oxidative coloring agent.

The following combinations of oxidation dye precursors of the developer type and of the coupler type are particularly preferred in the context of the present invention, where the amine compounds and the nitrogen heterocycles can also be present in the form of their physiologically acceptable salts:
p-toluoylenediamine/resorcinol;
p-toluoylenediamine/2-methylresorcinol;
p-toluoylenediamine/5-amino-2-methylphenol;
p-toluoylenediamine/3-aminophenol;
p-toluoylenediamine/2-(2,4-diaminophenoxy)ethanol;
p-toluoylenediamine/1,3-bis-(2,4-diaminophenoxy)propane;
p-toluoylenediamine/1-methoxy-2-amino-4-(2-hydroxyethylamino)benzene;
p-toluoylenediamine/2-amino-3-hydroxypyridine;
p-toluoylenediamine/1-naphthol;
2-(2-hydroxyethyl)-p-phenylenediamine/resorcinol;
2-(2-hydroxyethyl)-p-phenylenediamine/2-methylresorcinol;
2-(2-hydroxyethyl)-p-phenylenediamine/5-amino-2-methylphenol;
2-(2-hydroxyethyl)-p-phenylenediamine/3-aminophenol;
2-(2-hydroxyethyl)-p-phenylenediamine/2-(2,4-diaminophenoxy)ethanol;
2-(2-hydroxyethyl)-p-phenylenediamine/1,3-bis-(2,4-diaminophenoxy)propane;
2-(2-hydroxyethyl)-p-phenylenediamine/1-methoxy-2-amino-4-(2-hydroxyethylamino)benzene;
2-(2-hydroxyethyl)-p-phenylenediamine/2-amino-3-hydroxypyridine;
2-(2-hydroxyethyl)-p-phenylenediamine/1-naphthol;
2-methoxymethyl-p-phenylenediamine/resorcinol;
2-methoxymethyl-p-phenylenediamine/2-methylresorcinol;
2-methoxymethyl-p-phenylenediamine/5-amino-2-methylphenol;
2-methoxymethyl-p-phenylenediamine/3-aminophenol;
2-methoxymethyl-p-phenylenediamine/2-(2,4-diaminophenoxy)ethanol;
2-methoxymethyl-p-phenylenediamine/1,3-bis-(2,4-diaminophenoxy)propane;
2-methoxymethyl-p-phenylenediamine/1-methoxy-2-amino-4-(2-hydroxyethylamino)benzene;

2-methoxymethyl-p-phenylenediamine/2-amino-3-hydroxypyridine;
2-methoxymethyl-p-phenylenediamine/1-naphthol;
N-(4-amino-3-methylphenyl)-N-[3-(1H-imidazol-1-yl)propyl]amine/resorcinol;
N-(4-amino-3-methylphenyl)-N-[3-(1H-imidazol-1-yl)propyl]amine/2-methylresorcinol;
N-(4-amino-3-methylphenyl)-N-[3-(1H-imidazol-1-yl)propyl]amine/5-amino-2-methylphenol;
N-(4-amino-3-methylphenyl)-N-[3-(1H-imidazol-1-yl)propyl]amine/3-aminophenol;
N-(4-amino-3-methylphenyl)-N-[3-(1H-imidazol-1-yl)propyl]amine/2-(2,4-diaminophenoxy)ethanol;
N-(4-amino-3-methylphenyl)-N-[3-(1H-imidazol-1-yl)propyl]amine/1,3-bis-(2,4-diaminophenoxy)propane;
N-(4-amino-3-methylphenyl)-N-[3-(1H-imidazol-1-yl)propyl]amine/1-methoxy-2-amino-4-(2-hydroxyethylamino)benzene;
N-(4-amino-3-methylphenyl)-N-[3-(1H-imidazol-1-yl)propyl]amine/2-amino-3-hydroxypyridine;
N-(4-amino-3-methylphenyl)-N-[3-(1H-imidazol-1-yl)propyl]amine/1-naphthol;
4,5-diamino-1-(2-hydroxyethyl)pyrazole/resorcinol;
4,5-diamino-1-(2-hydroxyethyl)pyrazole/2-methylresorcinol;
4,5-diamino-1-(2-hydroxyethyl)pyrazole/5-amino-2-methylphenol;
4,5-diamino-1-(2-hydroxyethyl)pyrazole/3-aminophenol;
4,5-diamino-1-(2-hydroxyethyl)pyrazole/2-(2,4-diaminophenoxy)ethanol;
4,5-diamino-1-(2-hydroxyethyl)pyrazole/1,3-bis-(2,4-diaminophenoxy)propane;
4,5-diamino-1-(2-hydroxyethyl)pyrazole 1-methoxy-2-amino-4-(2-hydroxyethylamino)benzene;
4,5-diamino-1-(2-hydroxyethyl)pyrazole/2-amino-3-hydroxypyridine;
4,5-diamino-1-(2-hydroxyethyl)pyrazole/1-naphthol.

The combinations 4,5-diamino-1-(2-hydroxyethyl)pyrazole/3-aminophenol and p-toluoylenediamine/3-aminophenol are particularly preferred according to the present invention. The combination 4,5-diamino-1-(2-hydroxyethyl)pyrazole/3-aminophenol is extraordinarily preferred, in particular in terms of improving washing fastness.

In order to achieve balanced and subtle toning, it is preferred according to the present invention if further color-imparting components are contained in the coloring agent that is used in the method according to the present invention.

In a further embodiment, the agents used in step b) of this variant of the method according to the present invention can additionally contain at least one substantive dye. These are dyes that absorb directly onto the hair and do not require an oxidative process for formation of the color. Substantive dyes are usually nitrophenylenediamines, nitroaminophenols, azo dyes, anthraquinones, or indophenols.

A further preferred method according to the present invention is characterized in that the coloring and/or lightening agent applied in step b) is rinsed off the fibers after a period from about 5 to about 60 minutes, preferably about 15 to about 50 minutes, particularly preferably about 30 to about 45 minutes.

The coloring agent used in the method according to the present invention in step b) is produced from a two-component agent, where one component, namely composition (A), contains at least one alkalizing agent, at least one acylpyridinium derivative of formula (Acylpyr-I), and optionally the oxidation dye precursors and/or substantive dyes, and the other component, namely composition (B), contains the oxidizing agent or agents. The ready-to-use coloring and/or lightening agent for step b) is then produced by mixing the two components directly before the application step b). A separation into multi-component systems is advisable in particular when incompatibilities of the ingredients are expected or are a concern.

A further subject of the present Application is therefore a multi-component packaging unit (kit of parts) encompassing
(i) a first container (C1) having an agent containing at least one 4-morpholinomethyl-substituted silicone of formula (V),

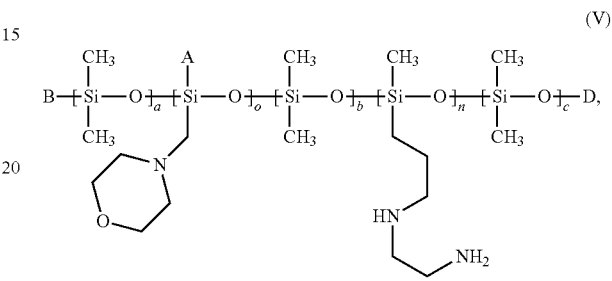

in which
A denotes a structural unit (I), (II), or (III) bound via —O—

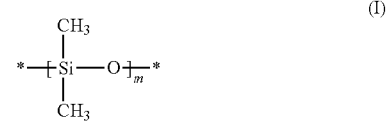

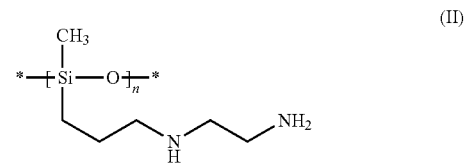

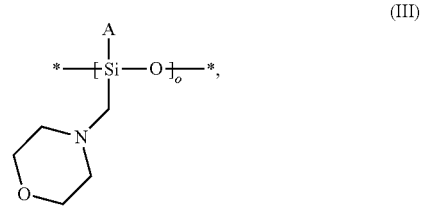

or an oligomeric or polymeric residue, bound via —O—, containing structural units of formulas (I), (II), or (III), or half of a connecting oxygen atom to a structural unit (III), or denotes —OH,
* denotes a bond to one of the structural units (I), (II), or (III), or denotes a terminal group B (Si-bound) or D (O-bound),
B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers from 0 to 990, with the provision that a+b+c>0, m, n, and o denote integers from 1 to 990, furthermore (ii) a second container (C2) having a composition (A) containing at least one alkalizing agent, (iii) and furthermore a third container (C3) having a composition (B) containing, in a cosmetic carrier, at least one oxidizing agent and at least one acylpyridinium derivative of formula (Acylpyr-I),

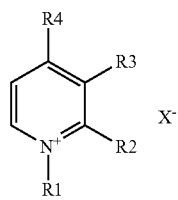

(Acylpyr-I), in which

R1 denotes a C$_1$ to C$_6$ alkyl group, a C$_2$ to C$_6$ alkenyl group, a C$_2$ to C$_6$ hydroxyalkyl group, a C$_1$ to C$_6$ alkoxy-C$_2$ to C$_6$ alkyl group, a carboxy C$_2$ to C$_6$ alkyl group, an aryl C$_1$ to C$_6$ alkyl group, a heteroaryl C$_1$ to C$_6$ alkyl group, an aryl group, or a heteroaryl group, R2, R3, and R4 mutually independently in each case denote hydrogen, a C$_1$ to C$_6$ alkyl group, a halogen atom, or a C$_1$ to C$_6$ acyl group, with the provision that at least one of the residues R2, R3, and R4 denotes a C$_1$ to C$_6$ acyl group, and X$^-$ denotes a physiologically acceptable anion.

The statements made above regarding preferred embodiments of the method according to the present invention also apply mutatis mutandis to the multi-component packaging units according to the present invention.

EXEMPLIFYING EMBODIMENTS

Example 1

Pretreatment with 4-morpholinomethyl-Substituted Silicones of Formula (V)

Hair skeins were immersed for one minute into an aqueous emulsion of a 4-morpholinomethyl-substituted silicone of formula (V) that contained 0.01 wt % 4-morpholinomethyl-substituted silicone(s) of formula (V) and 0.005 wt % branched Trideceth-5, furthermore 0.006 wt % glycerol, and water to 100 wt %, and then blow-dried.

Producing the Coloring Agent Applied in Method Step b)

TABLE 1

| Composition (A): color cream (quantities indicated in wt %) | |
|---|---|
| Toluene-2,5-Diamine Sulfate | 0.02 |
| 2-Amino-4-Hydroxyethylaminoanisole Sulfate (1-methoxy-2-amino-4-(2'-hydroxyethylamino)benzene sulfate) | 0.02 |
| 4-Amino-2-Hydroxytoluene | 0.01 |
| Cetearyl Alcohol | 14 |
| Glyceryl Stearate | 1.4 |
| Ammonium Hydroxide | 6.8 |
| Ceteareth-20 | 3.5 |
| Octyldodecanol | 1 |
| Sodium Laureth Sulfate | 0.5 |

TABLE 1-continued

| Composition (A): color cream (quantities indicated in wt %) | |
|---|---|
| 1,3-Butylene glycol | 3.5 |
| Sodium Cetearyl Sulfate | 1.0 |
| Oleic Acid | 0.1 |
| Perfume (Fragrance) | 0.5 |
| Potassium Stearate | 0.5 |
| Sodium Sulfite | 0.2 |
| Tetrasodium EDTA | 0.3 |
| Carbomer | 0.3 |
| Polyquaternium-39 (ex Merquat 3330) | 0.05 |
| Potassium Hydroxide | 0.08 |
| Ascorbic Acid | 0.02 |
| Linoleamidopropyl PG-Dimonium Chloride Phosphate | 0.1 |
| Sodium Sulfate | 0.1 |
| Citric Acid | 0.002 |
| CI 77891 (Titanium Dioxide) | 0.3 |
| Aqua (Water, Eau) | to 100 |

The composition (A) presented above was mixed at a 1:1 weight ratio either with the composition (B)-1 presented in Table 2 (=comparison oxidizing agent composition (B)), or with the composition (B)-2 presented in Table 2 (=oxidizing agent composition (B) having an acylpyridinium derivative content according to the present invention), to yield a respective ready-to-use coloring agent. The ready-to-use coloring agent was then applied onto the test skeins, specifically at a rate of 4 g coloring agent per gram of hair. The test skeins used were on the one hand ones that had previously been treated with the 4-morpholinomethyl-substituted silicone of formula (V), and on the other hand untreated test skeins.

The coloring agent remained on the skeins for 30 minutes in each case. The skeins were then rinsed out for 2 minutes using warm (32° C.) tap water at a flow rate of 0.5 liter per minute. The skeins were then combed three times before the actual combability measurements (10 comb strokes each on 20 skeins) were carried out.

TABLE 2

| Oxidizing agent compositions (B) (quantities indicated in wt %) | | |
|---|---|---|
| | (B)-1 | (B)-2 |
| 4-Acetyl-1-methylpyridinium-p-toluenesulfonate | — | 4.0 |
| Paraffinum Liquidum | 0.5 | 0.5 |
| Cetearyl Alcohol | 4.0 | 4.0 |
| Dipicolinic acid | 0.1 | 0.1 |
| Disodium Pyrophosphate | 0.1 | 0.1 |
| Potassium Hydroxide | 0.1 | 0.1 |
| 1,2-Propylene glycol | 1.0 | 1.0 |
| 1-Hydroxyethane-1,1-Diphosphonic Acid (Etidronic Acid) | 0.1 | 0.1 |
| Steartrimonium Chloride | 0.5 | 0.5 |
| Ceteareth-20 | 1.0 | 1.0 |
| H$_2$O$_2$ (active content) | 12.0 | 12.0 |
| Water | to 100 | to 100 |

TABLE 3

| Wet combability; combing work (mJ) | | |
|---|---|---|
| | Combing work (mJ) | Relative change (%) |
| (A) + (B)-1, without method step a) (comparison) | 1282 | 100 |
| (A) + (B)-2, without method step a) (comparison) | 1257 | 98 |
| (A) + (B)-1, with method step a) (comparison) | 802 | 63 |
| (A) + (B)-2, with method step a) (according to the present invention) | 705 | 55 |

TABLE 4

| | Split count after 20,000 comb strokes (proportion as %) | |
|---|---|---|
| | Split count (%) | Relative change (%) |
| (A) + (B)-1, without method step a) (comparison) | 1.5 | 100 |
| (A) + (B)-2, without method step a) (comparison) | 1.5 | 100 |
| (A) + (B)-1, with method step a) (comparison) | 1.3 | 87 |
| (A) + (B)-2, with method step a) (according to the present invention) | 1.1 | 73 |

As shown by the data presented in Tables 3 and 4, both the pretreatment using a 4-morpholinomethyl-substituted silicone of formula (V) alone and the use of an oxidizing agent composition (B) containing acylpyridinium derivative alone already have a positive effect on protection of the hair from oxidative damage: not only is combing work reduced by 20 resp. 27% (lower combing work being equivalent to less hair damage), but the number of splits caused by standardized test combing is reduced by 28 resp. 39%.

In contrast, the method according to the present invention, which combines pretreatment with the 4-morpholinomethyl-substituted silicones of formula (V) with the use of an oxidizing agent composition (B) having an acylpyridinium derivative content, brings a further very appreciable reduction in wet combing work and in the splitting rate.

The invention claimed is:

1. A method for oxidative lightening and/or coloring of keratinic fibers comprising the steps of:

a) applying onto the keratinic fibers a pretreatment agent that contains at least one 4-morpholinomethyl-substituted silicone of formula (V),

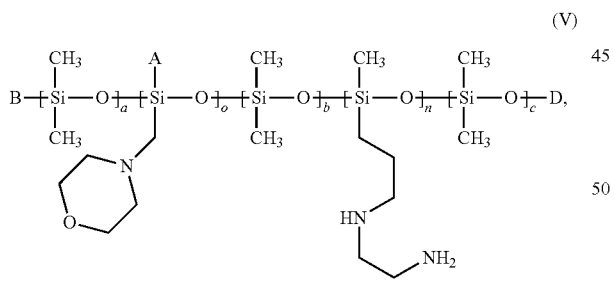

(V)

in which

A denotes a structural unit (I), (II), or (III) bound via —O—

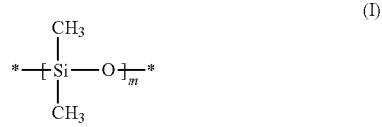

(I)

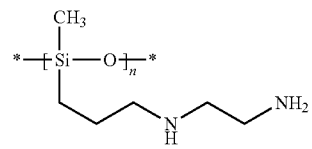

(II)

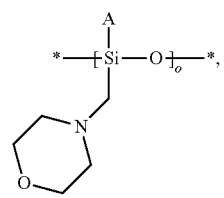

(III)

or an oligomeric or polymeric residue, bound via —O—, containing structural units (I), (II), or (III), or half of a connecting oxygen atom to the structural unit (III), or denotes —OH,

* denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers from 0 to 990, with the provision that a+b+c>0, m, n, and o denote integers from 1 to 990, b) subsequently, within a time span from about one second to about 24 hours after step a), applying a coloring and/or lightening agent onto the keratinic fibers, which coloring and/or lightening agent is obtained by mixing a composition (A) that contains at least one alkalizing agent with a composition (B) that contains, in a cosmetic carrier, at least one oxidizing agent, wherein the composition (B) contains at least one acylpyridinium derivative of formula (Acylpyr-I),

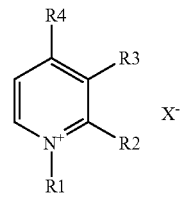

(Acylpyr-I), in which

R1 denotes a C$_1$ to C$_6$ alkyl group, a C$_2$ to C$_6$ alkenyl group, a C$_2$ to C$_6$ hydroxyalkyl group, a C$_1$ to C$_6$ alkoxy-C$_2$ to C$_6$ alkyl group, a carboxy C$_2$ to C$_6$ alkyl group, an aryl C$_1$ to C$_6$ alkyl group, a heteroaryl C$_1$ to C$_6$ alkyl group, an aryl group, or a heteroaryl group, R2, R3, and R4 mutually independently in each case denote hydrogen, a C$_1$ to C$_6$ alkyl group, a halogen atom, or a C$_1$ to C$_6$ acyl group, with the provision that at least one of the residues R2, R3, and R4 denotes a C$_1$ to C$_6$ acyl group, and X$^-$ denotes a physiologically acceptable anion.

2. The method according to claim 1, wherein applying in step a) comprises applying the pretreatment agent comprising at least one 4-morpholinomethyl-substituted silicone of formula (V) in which m>(n+o) resp. (a+b+c)>(n+o).

3. The method according to claim 2, wherein applying in step a) comprises applying the pretreatment agent comprising at least one 4-morpholinomethyl-substituted silicone of formula (V) in which m>200(n+o) resp. (a+b+c)>200(n+o).

4. The method according to claim 1, wherein applying in step a) comprises applying the pretreatment agent comprising, based on its weight, a 4-morpholinomethyl-substituted silicone in a total quantity from about 0.001 to about 5 wt %, based on the total weight of the pretreatment agent.

5. The method according to claim 4, wherein applying in step a) comprises applying the pretreatment agent comprising, based on its weight, a 4-morpholinomethyl-substituted silicone in a total quantity from about 0.02 to 0.1 wt %, based on the total weight of the pretreatment agent.

6. The method according to claim 1, wherein applying in step a) comprises applying the pretreatment agent comprising, based on its weight, at least one 4-morpholinomethyl-substituted silicone of formula (V) that comprises at least one of the structural units (I), (II), and (III), in a total quantity from about 0.001 to about 5 wt %, based on the total weight of the pretreatment agent.

7. The method according to claim 1, wherein applying in step a) comprises applying the pretreatment agent comprising a hydroxy-terminated 4-morpholinomethyl-substituted silicone in which a molar ratio of hydroxy to alkoxy is in a range from about 0.2:1 to about 0.4:1.

8. The method according to claim 1, wherein applying in step a) comprises applying the pretreatment agent comprising a 4-morpholinomethyl-substituted silicone of formula (V) with a weight-average molar mass in a range from about 2,000 to about 1,000,000 gmol$^{-1}$.

9. The method according to claim 8, wherein applying in step a) comprises applying the pretreatment agent comprising the 4-morpholinomethyl-substituted silicone of formula (V) with the weight-average molar mass in a range from about 5,000 to about 200,000 gmol$^{-1}$.

10. The method according to claim 1, wherein applying in step a) comprises applying the pretreatment agent comprising the 4-morpholinomethyl-substituted silicone of formula (V) that is present in a form of an oil-in-water emulsion in which a number-average size of silicone particles in the oil-in-water emulsion is in a range from about 3 to about 500 nm.

11. The method according to claim 10, wherein applying in step a) comprises applying the pretreatment agent comprising the 4-morpholinomethyl-substituted silicone of formula (V) that is present in the form of the oil-in-water emulsion in which the number-average size of the silicone particles in the oil-in-water emulsion is in the oil-in-water emulsion is in a range from 5 to 60 nm.

12. The method according to claim 1, wherein mixing with the composition (B) in step b) comprises mixing with the composition (B) having either R2 or R4 of the at least one acylpyridinium derivative of formula (Acylpyr-I) denoting a $C_1$ to $C_6$ acyl group.

13. The method according to claim 1, wherein mixing with the composition (B) in step b) comprises mixing with the composition (B) having the at least one acylpyridinium derivative of formula (Acylpyr-I) chosen from 4-acetyl-1-methylpyridinium-p-toluenesulfonate, 4-acetyl-1-methylpyridinium benzenesulfonate, 4-acetyl-1-methylpyridinium hydrogen sulfate, 4-acetyl-1-methylpyridinium acetate, 4-acetyl-1-allylpyridinium-p-toluenesulfonate, 4-acetyl-1-allylpyridinium benzenesulfonate, 4-acetyl-1-allylpyridinium hydrogen sulfate, 4-acetyl-1-allylpyridinium acetate, 2-acetyl-1-methylpyridinium-p-toluenesulfonate, 2-acetyl-1-methylpyridinium benzenesulfonate, 2-acetyl-1-methylpyridinium hydrogen sulfate, 2-acetyl-1-methylpyridinium acetate, 2-acetyl-1-allylpyridinium-p-toluenesulfonate, 2-acetyl-1-allylpyridinium benzenesulfonate, 2-acetyl-1-allylpyridinium hydrogen sulfate, and 2-acetyl-1-allylpyridinium acetate.

14. The method according to claim 1, wherein mixing with the composition (B) in step b) comprises mixing with the composition (B) having the at least one acylpyridinium derivative of formula (Acylpyr-I) present in a total quantity from about 0.001 to about 15 wt % based on the total weight of the coloring and/or lightening agent applied in method step b).

15. The method according to claim 1, wherein the pretreatment agent applied in method step a) is allowed to act on the keratinic fibers for a time span from about 2 seconds to about 120 minutes before at least one of the following method steps a) i), which are performed before method step b), is performed:
rinsing out the keratinic fibers;
drying the keratinic fibers with a towel;
allowing the keratinic fibers to air-dry;
blow-drying the keratinic fibers;
drying the keratinic fibers with a drying hood;
combinations of the aforementioned method steps,
wherein any of the drying operations occurs at a temperature from about 20° C. to about 150° C.

16. The method according to claim 15, wherein no rinsing out of the keratinic fibers occurs between application of the pretreatment agent performed in method step a) and the drying operation or operations.

17. The method according to claim 1, wherein mixing with the composition (B) in step b) comprises mixing with the composition (B) comprising at least one cosmetic oil in a total quantity from about 10 to about 80 wt %, based on a weight of composition (B).

18. The method according to claim 1, wherein in method step b) the coloring and/or lightening agent is applied onto the keratinic fibers, which coloring and/or lightening agent is obtained by mixing the composition (A), which comprises the at least one alkalizing agent, at least one oxidation dye precursor of the developer type, and at least one oxidation dye precursor of the coupler type, with the composition (B).

19. The method according to claim 1, wherein the method is for oxidative lightening and/or coloring of human hair.

20. A multi-component packaging unit (kit of parts) encompassing
a first container (C1) having an agent containing at least one 4-morpholinomethyl-substituted silicone of formula (V),

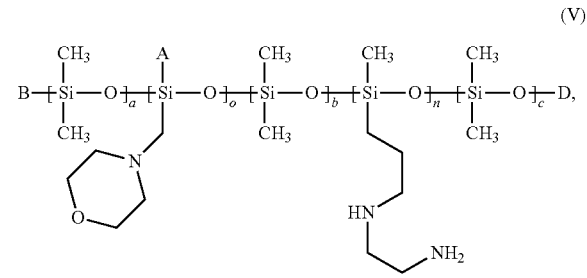

in which
A denotes a structural unit (I), (II), or (III) bound via —O—

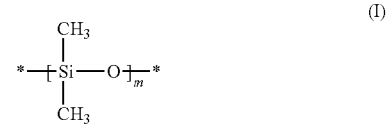

(II)

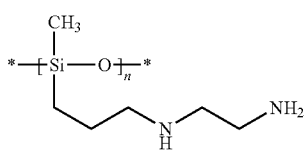

(III)

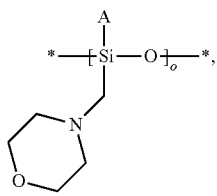

or an oligomeric or polymeric residue, bound via —O—, containing structural units (I), (II), or (III), or half of a connecting oxygen atom to the structural unit (III), or denotes —OH,

* denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers from 0 to 990, with the provision that a+b+c>0, m, n, and O denote integers from 1 to 990, furthermore a second container (C2) having a composition (A) containing at least one alkalizing agent, and furthermore a third container (C3) having a composition (B) containing, in a cosmetic carrier, at least one oxidizing agent and at least one acylpyridinium derivative of formula (Acylpyr-I),

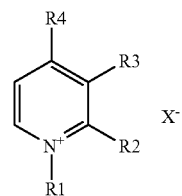

(Acylpyr-I), in which

R1 denotes a $C_1$ to $C_6$ alkyl group, a $C_2$ to $C_6$ alkenyl group, a $C_2$ to $C_6$ hydroxyalkyl group, a $C_1$ to $C_6$ alkoxy-$C_2$ to $C_6$ alkyl group, a carboxy $C_2$ to $C_6$ alkyl group, an aryl $C_1$ to $C_6$ alkyl group, a heteroaryl $C_1$ to $C_6$ alkyl group, an aryl group, or a heteroaryl group, R2, R3, and R4 mutually independently in each case denote hydrogen, a $C_1$ to $C_6$ alkyl group, a halogen atom, or a $C_1$ to $C_6$ acyl group, with the provision that at least one of the residues R2, R3, and R4 denotes a $C_1$ to $C_6$ acyl group, and $X^-$ denotes a physiologically acceptable anion.

* * * * *